(12) United States Patent
Hale Horton et al.

(10) Patent No.: US 8,648,220 B2
(45) Date of Patent: Feb. 11, 2014

(54) PROCESS FOR PRODUCING ETHANOL USING A CRUDE VINYL ACETATE FEED

(75) Inventors: Trinity Hale Horton, Houston, TX (US); Victor J. Johnston, Houston, TX (US)

(73) Assignee: Celanese International Corporation, Dallas, TX (US)

( * ) Notice: Subject to any disclaimer, the term of this patent is extended or adjusted under 35 U.S.C. 154(b) by 295 days.

(21) Appl. No.: 13/270,838

(22) Filed: Oct. 11, 2011

(65) Prior Publication Data

US 2013/0090501 A1    Apr. 11, 2013

(51) Int. Cl.
C07C 29/149    (2006.01)

(52) U.S. Cl.
USPC .................................................... 568/885

(58) Field of Classification Search
USPC .................................................... 568/885
See application file for complete search history.

(56) References Cited

U.S. PATENT DOCUMENTS

| | | |
|---|---|---|
| 2,882,244 A | 4/1959 | Milton |
| 3,130,007 A | 4/1964 | Breck |
| 4,379,028 A | 4/1983 | Berg et al. |
| 4,569,726 A | 2/1986 | Berg et al. |
| 4,994,608 A | 2/1991 | Torrence et al. |
| 5,001,259 A | 3/1991 | Smith et al. |
| 5,026,908 A | 6/1991 | Smith et al. |
| 5,144,068 A | 9/1992 | Smith et al. |
| 5,185,308 A | 2/1993 | Bartley et al. |
| RE35,377 E | 11/1996 | Steinberg et al. |
| 5,599,976 A | 2/1997 | Scates et al. |
| 5,691,267 A | 11/1997 | Nicolau et al. |
| 5,821,111 A | 10/1998 | Gaddy et al. |
| 5,993,610 A | 11/1999 | Berg |
| 6,040,474 A | 3/2000 | Jobson et al. |
| 6,114,571 A | 9/2000 | Abel et al. |
| 6,143,930 A | 11/2000 | Singh et al. |
| 6,232,352 B1 | 5/2001 | Vidalin et al. |
| 6,375,807 B1 | 4/2002 | Nieuwoudt et al. |
| 6,476,261 B2 | 11/2002 | Ellis et al. |
| 6,509,180 B1 | 1/2003 | Verser et al. |
| 6,603,038 B1 | 8/2003 | Hagemeyer et al. |
| 6,627,770 B1 | 9/2003 | Cheung et al. |
| 6,657,078 B2 | 12/2003 | Scates et al. |
| 6,685,754 B2 | 2/2004 | Kindig et al. |
| 6,696,596 B1 | 2/2004 | Herzog et al. |
| 6,852,877 B1 | 2/2005 | Zeyss et al. |
| 6,927,048 B2 | 8/2005 | Verser et al. |
| 7,005,541 B2 | 2/2006 | Cheung et al. |
| 7,074,603 B2 | 7/2006 | Verser et al. |
| 7,115,772 B2 | 10/2006 | Picard et al. |
| 7,208,624 B2 | 4/2007 | Scates et al. |
| 7,351,559 B2 | 4/2008 | Verser et al. |
| 7,507,562 B2 | 3/2009 | Verser et al. |
| 7,601,865 B2 | 10/2009 | Verser et al. |
| 7,608,744 B1 | 10/2009 | Johnston et al. |
| 7,682,812 B2 | 3/2010 | Verser et al. |
| 7,700,801 B2 | 4/2010 | Warner et al. |
| 7,863,489 B2 | 1/2011 | Johnston et al. |
| 7,884,253 B2 | 2/2011 | Stites et al. |
| 7,888,082 B2 | 2/2011 | Verser et al. |
| 2008/0193989 A1 | 8/2008 | Verser et al. |
| 2009/0069609 A1 | 3/2009 | Kharas et al. |
| 2009/0281354 A1 | 11/2009 | Mariansky et al. |
| 2010/0029995 A1 | 2/2010 | Johnston et al. |
| 2010/0030001 A1 | 2/2010 | Chen et al. |
| 2010/0030002 A1 | 2/2010 | Johnston et al. |
| 2010/0168467 A1 | 7/2010 | Johnston et al. |
| 2010/0197485 A1 | 8/2010 | Johnston et al. |
| 2011/0190551 A1 | 8/2011 | Jevtic et al. |

FOREIGN PATENT DOCUMENTS

WO    WO 2009/063176    5/2009

OTHER PUBLICATIONS

International Search Report and Written Opinion mailed on Dec. 19, 2012 in corresponding International Application No. PCT/US2012/059638.

*Primary Examiner* — Elvis O Price

(57) ABSTRACT

Converting a crude vinyl acetate feed to ethanol by hydrogenating the acetic acid and ethyl acetate in the crude vinyl acetate feed. The crude vinyl acetate feed may comprise acetic acid and/or ethyl acetate, as well as vinyl acetate and minor amounts of vinyl propionate. The crude vinyl acetate feed may be obtained from an azeotrope column as either a sidestream or a bottom stream in a vinyl acetate production process.

25 Claims, 5 Drawing Sheets

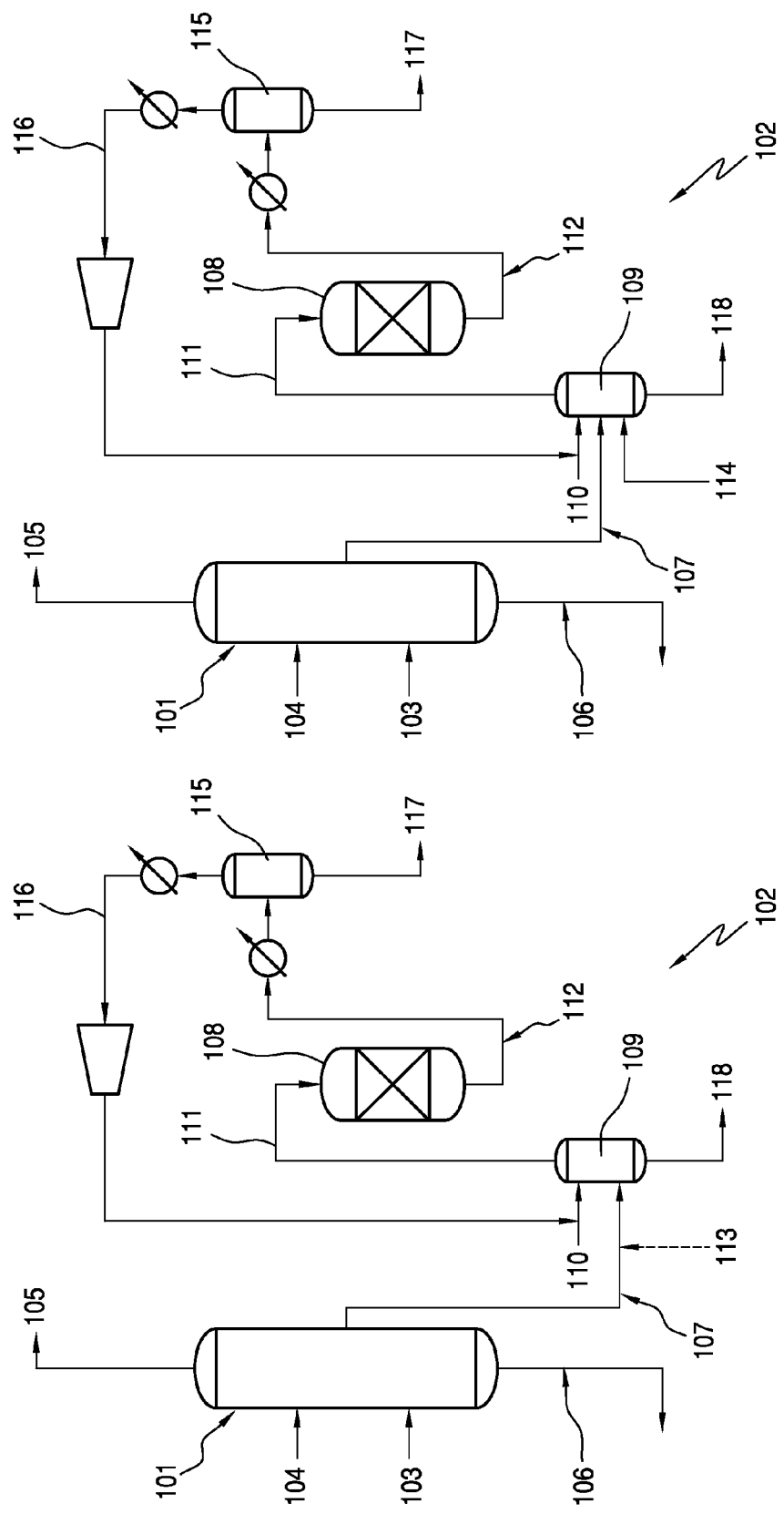

US 8,648,220 B2

PROCESS FOR PRODUCING ETHANOL USING A CRUDE VINYL ACETATE FEED

FIELD OF THE INVENTION

The present invention relates generally to hydrogenation processes for producing ethanol and in particular, to processes for producing ethanol product by hydrogenating a crude vinyl acetate feed.

BACKGROUND OF THE INVENTION

Ethanol for industrial use is conventionally produced from petrochemical feed stocks, such as oil, natural gas, or coal, from feed stock intermediates, such as syngas, or from starchy materials or cellulose materials, such as corn or sugar cane. Conventional methods for producing ethanol from petrochemical feed stocks, as well as from cellulose materials, include the acid-catalyzed hydration of ethylene, methanol homologation, direct alcohol synthesis, and Fischer-Tropsch synthesis. Instability in petrochemical feed stock prices contributes to fluctuations in the cost of conventionally produced ethanol, making the need for alternative sources of ethanol production all the greater when feed stock prices rise. Starchy materials, as well as cellulose material, are converted to ethanol by fermentation. However, fermentation is typically used for consumer production of ethanol, which is suitable for fuels or human consumption. In addition, fermentation of starchy or cellulose materials competes with food sources and places restraints on the amount of ethanol that can be produced for industrial use.

Ethanol production via the reduction of alkanoic acids and/or other carbonyl group-containing compounds has been widely studied, and a variety of combinations of catalysts, supports, and operating conditions have been mentioned in the literature. For example, EP02060553 describes a process for converting hydrocarbons to ethanol involving converting the hydrocarbons to ethanoic acid and hydrogenating the ethanoic acid to ethanol. The stream from the hydrogenation reactor is separated to obtain an ethanol stream and a stream of acetic acid and ethyl acetate, which is recycled to the hydrogenation reactor.

WO2009063176 describes a process for the conversion of acetic acid into ethanol involving introducing acetic acid and hydrogen into a primary hydrogenation unit and reacting to produce ethanol and ethyl acetate, introducing the ethyl acetate created with hydrogen into a secondary hydrogenation unit and reacting to produce ethanol, and recovering the ethanol.

Even in view of these teachings, the need remains for improved processes for producing ethanol by hydrogenation.

SUMMARY OF THE INVENTION

In a first embodiment, the present invention is directed to a process for producing ethanol comprising separating at least a portion of a crude vinyl acetate mixture to yield a vinyl acetate product stream and a by-product stream comprising acetic acid, ethyl acetate, and vinyl acetate; hydrogenating at least a portion of the by-product stream in the presence of a catalyst to produce a crude ethanol product; and recovering ethanol from the crude ethanol product.

In a second embodiment, the present invention is directed to a process for producing ethanol comprising providing a by-product stream comprising acetic acid, ethyl acetate, and vinyl acetate; hydrogenating at least a portion of the by-product stream in the presence of a catalyst to produce a crude ethanol product; and recovering ethanol from the crude ethanol product.

In a third embodiment, the present invention is directed to a process for producing ethanol comprising separating at least a portion of a crude vinyl acetate mixture in an azeotrope column to yield a vinyl acetate product stream and sidestream comprising acetic acid and ethyl acetate; hydrogenating at least a portion of the sidestream in the presence of a catalyst to produce a crude ethanol product; and recovering ethanol from the crude ethanol product.

In a fourth embodiment, the present invention is directed to a process for producing ethanol comprising separating at least a portion of a crude vinyl acetate mixture in an azeotrope column to yield a vinyl acetate product stream and bottom stream comprising ethyl acetate and acetic acid; hydrogenating at least a portion of the bottom stream in the presence of a catalyst to produce a crude ethanol product; and recovering ethanol from the crude ethanol product.

BRIEF DESCRIPTION OF DRAWINGS

The invention is described in detail below with reference to the appended drawings, wherein like numerals designate similar parts.

FIG. 2A is a schematic diagram of a sidestream from an azeotrope column in a vinyl acetate being fed to a hydrogenation reaction zone in accordance with an embodiment of this invention.

FIG. 2B is a schematic diagram of a sidestream from an azeotrope column in a vinyl acetate being co-fed along with an feed stream of alkanoic acid and/or esters to a hydrogenation reaction zone in accordance with an embodiment of this invention.

DETAILED DESCRIPTION OF THE INVENTION

The present invention relates to processes for producing ethanol by hydrogenating a crude vinyl acetate feed. The crude vinyl acetate feed comprises alkanoic acid and/or esters thereof, in particular acetic acid and/or ethyl acetate, and at least a portion of the crude vinyl acetate feed is obtained from a by-product stream in vinyl acetate production process. Vinyl acetate production processes may involve oxidative addition of acetic acid to ethylene. In one embodiment, the portion obtained from a vinyl acetate production process may comprise ethyl acetate and/or acetic acid, and optionally may comprise vinyl acetate and/or water. In vinyl acetate production processes, these by-product streams require additional purging, treating, and recycling. For example, when recycling the by-product stream, heavy components tend to build up in the vinyl acetate process. Advantageously, the present invention may use a by-product stream from a vinyl acetate production process to produce a crude ethanol product and thus reduce the need for purging, treating, and recycling the by-product streams. The crude ethanol product may be separated to produce ethanol.

At least one by-product streams from the azeotrope column may be introduced into the hydrogenation process, along with additional amounts of alkanoic acids and/or esters thereof, to form ethanol. Without being bound by theory the vinyl acetate in the by-product stream, even in minor amounts, may be hydrogenated to ethyl acetate subsequently reacted to form ethanol.

Vinyl Acetate Azeotrope Column

Vinyl acetate production processes are widely used. Industrial processes use a palladium based catalyst, such as a palladium-gold catalyst, including those catalysts described in U.S. Pat. Nos. 5,185,308; 5,691,267; 6,114,571; 6,603,038; and 6,852,877 the entire contents and disclosure of which are hereby incorporated by reference.

The reaction mixture may comprise vinyl acetate, acetic acid, ethyl acetate, and water. In some embodiments, vinyl acetate and ethyl acetate may be co-produced, as described in U.S. Pat. No. 7,700,801, the entire contents and disclosure of which is hereby incorporated by reference. Suitable separation systems for vinyl acetate processes include those described in U.S. Pat. Nos. 6,040,474; 6,476,261; and 6,696,596, the entireties of which are incorporated herein by reference.

Figure 1B:
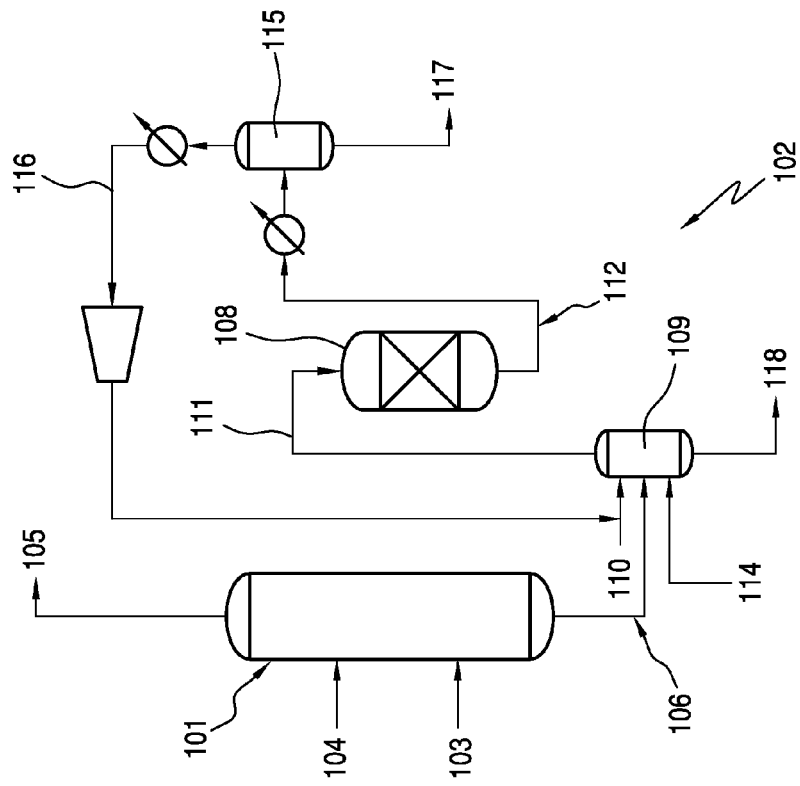
FIG. 1B is a schematic diagram of a bottom stream from an azeotrope column in a vinyl acetate being co-fed along with an feed stream of alkanoic acid and/or esters thereof to a hydrogenation reaction zone in accordance with an embodiment of this invention.
Figure 1A:
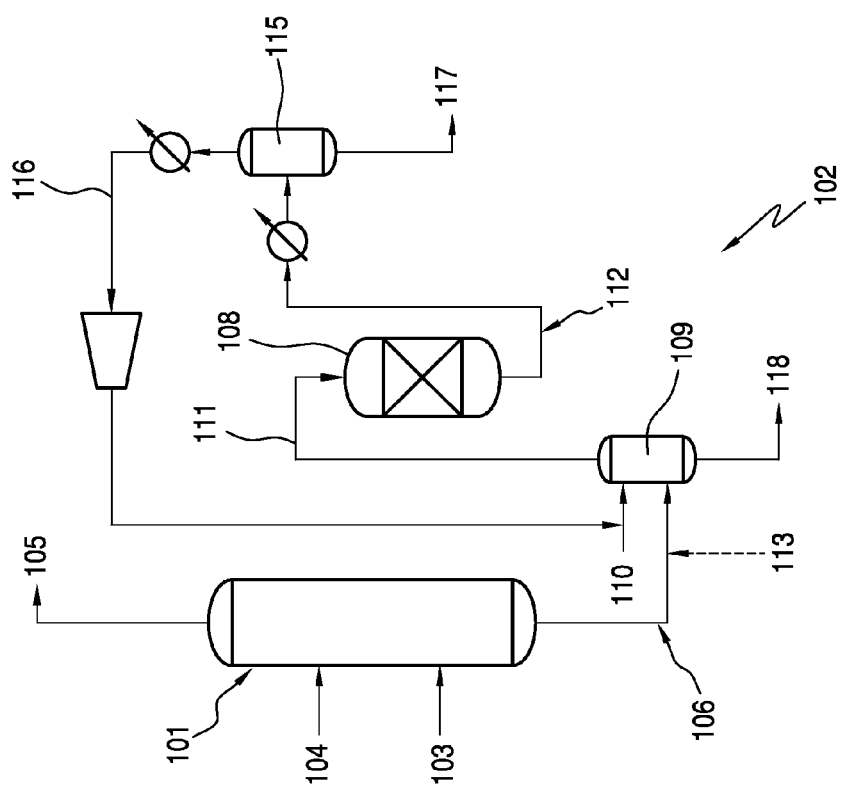
FIG. 1A is a schematic diagram of a bottom stream from an azeotrope column in a vinyl acetate being fed to a hydrogenation reaction zone in accordance with an embodiment of this invention.

To recover vinyl acetate the reaction mixture is separated in an azeotrope column to yield a vinyl acetate-water overhead that may be further dehydrated as needed. In some embodiments, as shown in FIGS. 1A and 1B, the azeotrope column may produce a bottom stream comprising acetic acid, ethyl acetate, and water without a sidestream. In other embodiments, as shown in FIGS. 2A and 2B, the azeotrope column may produce a sidestream comprising acetic acid and ethyl acetate and a bottom stream comprising acetic acid and water.

In addition to ethyl acetate, acetic acid, and water, the sidestream and/or bottom stream may also contain vinyl acetate, preferably in minor amounts. In one embodiment, the amount of vinyl acetate in sidestream and/or bottom stream may be less than 35 wt. %, e.g., less than 20 wt. %, or less than 10 wt. %. In terms of ranges, the vinyl acetate concentration may range from 0.01 to 35 wt. %, e.g., from 0.1 to 20 wt. %, or from 1 to 10 wt. %. In addition to vinyl acetate, the by-product stream may also comprise higher molecular weight acetates and/or polymers. In one embodiment, the by-product stream may comprise less than 2 wt. % vinyl proprionate, e.g., less than 1 wt. % or less than 0.5 wt. %. In some embodiments, very low concentrations of vinyl proprionate of less than 400 wppm may be present in the by-product stream. For purposes of the present invention, the sidestream and/or bottom stream may be referred to as by-product streams because a separate vinyl acetate enriched stream is withdrawn as the product.

In one embodiment, the by-product stream may be further treated to remove vinyl acetate prior to hydrogenation. The treated by-product stream may comprise acetic acid and/or ethyl acetate.

FIGS. 1A, 1B, 2A, and 2B are schematic diagrams of an azeotrope column 101 from a vinyl acetate process that produces at least one by-product streams to be introduced into a hydrogenation reaction zone 102. A crude vinyl acetate mixture, comprising vinyl acetate, acetic acid, ethyl acetate, and optionally water, is fed via line 103 to azeotrope column 101. In one embodiment, the crude vinyl acetate mixture comprises vinyl acetate in an amount from 1 to 35 wt. %, e.g., from 5 to 30 wt. %. In addition, an azeotrope agent, such as water, ethyl acetate, or a mixture thereof, may be introduced via line 104. Azeotrope column 101 recovers an azeotrope of vinyl acetate and water in the overhead stream 105, also referred to as the vinyl acetate product stream. Preferably a majority of the vinyl acetate fed to azeotrope column 101 is recovered in the overhead stream 105. Overhead stream 105 may be further separated to recover vinyl acetate. In some embodiments, aldehyde may also concentrate in the overhead stream 105.

In FIGS. 1A and 1B, azeotrope column also forms a bottom stream 106, e.g. by-product stream, comprising acetic acid, ethyl acetate, water, and minor amounts of vinyl acetate. Although the composition of bottom stream 106 may vary depending on the vinyl acetate production process, in one exemplary embodiment, bottom stream 106 may comprise less than 98 wt. % acetic acid, e.g., less than 95 wt. %, or less than 90 wt. %. Bottom stream 106 may comprise at least 50 wt. % acetic acid. In addition, bottom stream 106 may comprise from 0.01 to 50 wt. % ethyl acetate, e.g., from 0.1 to 35 wt. % ethyl acetate or from 1 to 15 wt. % ethyl acetate. The balance of bottom stream may comprise water.

In FIGS. 2A and 2B, in addition to bottom stream 106, azeotrope column 101 also forms a sidestream 107, e.g. by-product stream. In one preferred embodiment, sidestream 107 is introduced into hydrogenation reaction zone 102 and bottom stream 106 may be purged or retained as necessary in the vinyl acetate production process. In embodiments of the present invention, sidestream 107 comprises acetic acid, ethyl acetate, and minor amounts of water, e.g., less than 1 wt. %. For example, sidestream 107 may comprise acetic acid in an amount from 30 to 80 wt. %, e.g., from 40 to 75 wt. % or from 50 to 70 wt. %. Sidestream 107 may also comprise ethyl acetate in an amount from 0.1 to 25 wt. %, e.g., from 0.5 to 15 wt. % or from 1 to 10 wt. %. Vinyl acetate may also be present in sidestream 107, and vinyl acetate when present is an amount from 0.01 to 35 wt. %, e.g., from 0.1 to 30 wt. % or from 1 to 20 wt. %.

When sidestream 107 is withdrawn from azeotrope column 101 in FIGS. 2A and 2B, bottom stream 106 may comprise a greater portion of acetic acid. In one exemplary embodiment, bottom stream 106 may comprise from 5 to 98 wt. % acetic acid, e.g., 10 to 95 wt. %, or from 20 to 90 wt. %. Water may also be present in bottom stream 106. Preferably, when a sidestream 107 is withdrawn, bottom stream 106 may also be deficiency in ethyl acetate and comprise less than 5 wt. % ethyl acetate, e.g., less than 2.5 wt. %, or less than 1 wt. %. In one embodiment, bottom stream 106 may also comprise heavy compounds and may be separately treated to remove those compounds.

In one embodiment, the crude vinyl acetate feed comprises the by-product stream and may be fed to a hydrogenation reactor 108 to produce ethanol. As shown in FIG. 1A, bottom stream 106, or a portion thereof, may be introduced to a vaporizer 109 along with hydrogen via line 110. In FIG. 2A, sidestream 107, or a portion thereof, may be introduced to a vaporizer 109 along with hydrogen via line 110. Vaporizer 109 produces a vapor feed stream in line 111 that is directed to reactor 108. The temperature of the vapor feed stream in line 111 is preferably from 100° C. to 350° C., e.g., from 120° C. to 310° C. or from 150° C. to 300° C. Although line 111 is shown as being directed to the top of reactor 108, line 111 may be directed to the side, upper portion, or bottom of reactor 108. In addition, any feed that is not vaporized is removed from vaporizer 109 and purged via a blowdown stream 118. Blowdown stream 118 may comprise high molecular weight acetates and/or polymers in by-product stream from the vinyl acetate process.

Reactor 108 contains the catalyst that is used in the hydrogenation of the carboxylic acid, preferably acetic acid. In one embodiment, one or more guard beds (not shown) may be used upstream of the reactor, optionally upstream of the vaporizer 109, to protect the catalyst from poisons or undesirable impurities contained in the feed or return/recycle streams. Such guard beds may be employed in the vapor or liquid streams. Suitable guard bed materials may include, for example, carbon, silica, alumina, ceramic, or resins. In one aspect, the guard bed media is functionalized, e.g., silver functionalized, to trap particular species such as sulfur or halogens. During the hydrogenation process, a crude ethanol product stream is withdrawn, preferably continuously, from reactor 108 via line 112.

In one embodiment, the by-product stream, e.g., bottom stream 106 in FIG. 1A or sidestream 107 in FIG. 2A, may be introduced to vaporizer 109 without any additional alkanoic acids and/or esters thereof.

In one optional embodiment as shown in FIGS. 1A and 2A, the by-product stream from the vinyl acetate process may be further enriched with alkanoic acids and/or esters thereof, such as acetic acid and/or ethyl acetate via line 113. Depending on the concentration ethyl acetate or acetic acid in the by-product stream it may be desirable to enrich the by-product stream such at that the total concentration of ethyl acetate and/or acetic acid is greater than 70 wt. %, e.g., greater than 85 wt. % or greater than 90 wt. %. For purposes of the present invention, the enriched by-product stream may be hydrogenated to form ethanol.

Acetic Acid and/or Ethyl Acetate Feed Streams

In other embodiments as shown in FIGS. 1B and 2B, the by-product stream may be combined with a feed stream of acetic acid and/or ethyl acetate in line 114. For purposes of the present invention, the combined by-product stream and feed stream may also be referred as a crude vinyl acetate feed. The by-product stream, e.g., bottom stream 106 or sidestream 107, and acetic acid and/or ethyl acetate in line 114 may be separately fed to vaporizer 109 and directed to reactor 108 to form a crude ethanol product stream in line 112.

The weight ratio of the by-product stream, e.g., bottom stream 106 or sidestream 107, to feed stream in line 114 may be 100:1 to 1:100, e.g., from 50:1 to 1:50 or from 20:1 to 1:20. It may be preferred to combine the streams in a weight ratio that dilutes the by-product stream and may be greater than 1:20, e.g., greater than 1:50 or even greater than 1:100. Diluting the by-product stream may be necessary when the concentration of acetic acid and/or ethyl acetate in the by-product is less than the other concentration of the other components. Further, when the feed stream is of poor quality, it may be desirable to dilute the feed stream with the by-product stream and the weight ratio may be greater than 20:1, e.g., greater than 50:1 or even greater than 100:1.

Crude ethanol product in line 112 may be condensed and fed to a separator 115, which, in turn, provides a vapor stream 116 and a liquid stream 117. In some embodiments, separator 115 may comprise a flasher or a knockout pot. The separator 115 may operate at a temperature from 20° C. to 250° C., e.g., from 30° C. to 225° C. or from 60° C. to 200° C. The pressure of separator 115 may be from 50 kPa to 2000 kPa, e.g., from 75 kPa to 1500 kPa or from 100 kPa to 1000 kPa. Optionally, the crude ethanol product in line 112 may pass through one or more membranes to separate hydrogen and/or other non-condensable gases.

The vapor stream 116 exiting separator 115 may comprise hydrogen and hydrocarbons, and may be purged and/or returned to reaction zone 102. When returned to reaction zone 102, vapor stream 116 is combined with the hydrogen feed 110 and co-fed to vaporizer 109. In some embodiments, the returned vapor stream 116 may be compressed before being combined with hydrogen feed 110 and initially fed to reaction zone 102. Ethanol may be recovered from liquid stream 117 using several different separation processes as described below.

In further embodiments of the present invention, a portion of the sidestream 107 and bottom stream 106 may be combined and jointly fed to vaporizer 109. In addition, although not shown, optional bottom stream 106 from FIGS. 2A and 2B may be fed to vaporizer 109 and sidestream 107 may be purged or retained as necessary in the vinyl acetate production process.

The raw materials, including hydrogen and those materials used to produce optional feed stream 113 in FIGS. 1A and 2A, and feed stream 114 in FIGS. 1B and 2B, in connection with the process of this invention may be derived from any suitable source including natural gas, petroleum, coal, biomass, and so forth. As examples, acetic acid may be produced via methanol carbonylation, acetaldehyde oxidation, ethylene oxidation, oxidative fermentation, and anaerobic fermentation. Methanol carbonylation processes suitable for production of acetic acid are described in U.S. Pat. Nos. 7,208,624; 7,115,772; 7,005,541; 6,657,078; 6,627,770; 6,143,930; 5,599,976; 5,144,068; 5,026,908; 5,001,259; and 4,994,608, the entire disclosures of which are incorporated herein by reference. Optionally, the production of ethanol may be integrated with such methanol carbonylation processes.

As petroleum and natural gas prices fluctuate becoming either more or less expensive, methods for producing acetic acid and intermediates such as methanol and carbon monoxide from alternate carbon sources have drawn increasing interest. In particular, when petroleum is relatively expensive, it may become advantageous to produce acetic acid from synthesis gas ("syngas") that is derived from more available carbon sources. U.S. Pat. No. 6,232,352, the entirety of which is incorporated herein by reference, for example, teaches a method of retrofitting a methanol plant for the manufacture of acetic acid. By retrofitting a methanol plant, the large capital costs associated with CO generation for a new acetic acid plant are significantly reduced or largely eliminated. All or part of the syngas is diverted from the methanol synthesis loop and supplied to a separator unit to recover CO, which is then used to produce acetic acid. In a similar manner, hydrogen for the hydrogenation step may be supplied from syngas.

In some embodiments, some or all of the raw materials for the above-described acetic acid hydrogenation process may be derived partially or entirely from syngas. For example, the acetic acid may be formed from methanol and carbon monoxide, both of which may be derived from syngas. The syngas may be formed by partial oxidation reforming or steam reforming, and the carbon monoxide may be separated from syngas. Similarly, hydrogen that is used in the step of hydrogenating the acetic acid to form the crude ethanol product may be separated from syngas. The syngas, in turn, may be derived from variety of carbon sources. The carbon source, for example, may be selected from the group consisting of natural gas, oil, petroleum, coal, biomass, and combinations thereof. Syngas or hydrogen may also be obtained from bio-derived methane gas, such as bio-derived methane gas produced by landfills or agricultural waste.

In another embodiment, the acetic acid used in the hydrogenation step may be formed from the fermentation of biomass. The fermentation process preferably utilizes an acetogenic process or a homoacetogenic microorganism to ferment sugars to acetic acid producing little, if any, carbon dioxide as a by-product. The carbon efficiency for the fermentation process preferably is greater than 70%, greater than 80% or greater than 90% as compared to conventional yeast processing, which typically has a carbon efficiency of about 67%. Optionally, the microorganism employed in the fermentation process is of a genus selected from the group consisting of *Clostridium, Lactobacillus, Moorella, Thermoanaerobacter, Propionibacterium, Propionispera, Anaerobiospirillum*, and *Bacteriodes*, and in particular, species selected from the group consisting of *Clostridium formicoaceticum, Clostridium butyricum, Moorella thermoacetica, Thermoanaerobacter kivui, Lactobacillus delbrukii, Propionibacterium acidipropionici, Propionispera arboris, Anaerobiospirillum succinicproducens, Bacteriodes amylophilus* and *Bacteriodes ruminicola*. Optionally in this process, all or a portion of the unfermented residue from the biomass, e.g., lignans, may be gasified to form hydrogen that may be used in the hydrogenation step of the present invention. Exemplary fermentation processes for forming acetic acid are disclosed in U.S. Pat. Nos. 6,509,180; 6,927,048; 7,074,603; 7,507,562; 7,351,559; 7,601,865; 7,682,812; and 7,888,082, the entireties of which are incorporated herein by reference. See also U.S. Pub. Nos. 2008/0193989 and 2009/0281354, the entireties of which are incorporated herein by reference.

Examples of biomass include, but are not limited to, agricultural wastes, forest products, grasses, and other cellulosic material, timber harvesting residues, softwood chips, hardwood chips, tree branches, tree stumps, leaves, bark, sawdust, off-spec paper pulp, corn, corn stover, wheat straw, rice straw, sugarcane bagasse, switchgrass, miscanthus, animal manure, municipal garbage, municipal sewage, commercial waste, grape pumice, almond shells, pecan shells, coconut shells, coffee grounds, grass pellets, hay pellets, wood pellets, cardboard, paper, plastic, and cloth. See, e.g., U.S. Pat. No. 7,884,253, the entirety of which is incorporated herein by reference. Another biomass source is black liquor, a thick, dark liquid that is a byproduct of the Kraft process for transforming wood into pulp, which is then dried to make paper. Black liquor is an aqueous solution of lignin residues, hemicellulose, and inorganic chemicals.

U.S. Pat. No. RE 35,377, also incorporated herein by reference, provides a method for the production of methanol by conversion of carbonaceous materials such as oil, coal, natural gas and biomass materials. The process includes hydrogasification of solid and/or liquid carbonaceous materials to obtain a process gas which is steam pyrolyzed with additional natural gas to form synthesis gas. The syngas is converted to methanol which may be carbonylated to acetic acid. The method likewise produces hydrogen which may be used in connection with this invention as noted above. U.S. Pat. No. 5,821,111, which discloses a process for converting waste biomass through gasification into synthesis gas, and U.S. Pat. No. 6,685,754, which discloses a method for the production of a hydrogen-containing gas composition, such as a synthesis gas including hydrogen and carbon monoxide, are incorporated herein by reference in their entireties.

Alternatively, acetic acid in vapor form may be taken directly as crude product from the flash vessel of a methanol carbonylation unit of the class described in U.S. Pat. No. 6,657,078, the entirety of which is incorporated herein by reference. The crude vapor product, for example, may be fed directly to the first reaction zone of the present invention without the need for condensing the acetic acid and light ends or removing water, saving overall processing costs.

The feed stream combined or enriched with the by-product stream, may also comprise other carboxylic acids, esters, and anhydrides, as well as acetaldehyde and acetone. Preferably, a suitable feed stream comprises one or more of the compounds selected from the group consisting of acetic acid, acetic anhydride, ethyl acetate, acetaldehyde, and mixtures thereof. These other compounds may also be hydrogenated in the processes of the present invention. In some embodiments, the presence of carboxylic acids, such as propanoic acid or its anhydride, may be beneficial in producing propanol. Water may also be present in the feed stream.

Hydrogenation Process

The crude vinyl acetate feed may be vaporized at the reaction temperature, following which the vaporized vinyl acetate feed, and in particular acetic acid, may be fed along with hydrogen in an undiluted state or diluted with a relatively inert carrier gas, such as nitrogen, argon, helium, carbon dioxide and the like. For reactions run in the vapor phase, the temperature should be controlled in the system such that it does not fall below the dew point of acetic acid. In one embodiment, the crude vinyl acetate feed may be vaporized at the boiling point of acetic acid at the particular pressure, and then the vaporized vinyl acetate feed may be further heated to the reactor inlet temperature. In another embodiment, the crude vinyl acetate feed is mixed with other gases before vaporizing, followed by heating the mixed vapors up to the reactor inlet temperature. Preferably, the crude vinyl acetate feed is transferred to the vapor state by passing hydrogen and/or recycle gas through the crude vinyl acetate feed at a temperature at or below 125° C., followed by heating of the combined gaseous stream to the reactor inlet temperature.

The hydrogen reaction may consume two moles of hydrogen per mole of acetic acid to produce one mole of ethanol. In embodiments of the present invention, the actual molar ratio of hydrogen to acetic acid in the feed stream may vary from about 100:1 to 1:100, e.g., from 50:1 to 1:50, from 20:1 to 1:2, or from 12:1 to 1:1. Most preferably, the molar ratio of hydrogen to acetic acid is greater than 2:1, e.g., greater than 4:1 or greater than 8:1.

In the hydrogenation reaction zone, the hydrogenation of crude vinyl acetate feed to form ethanol is preferably conducted in the presence of a hydrogenation catalyst. Suitable hydrogenation catalysts include catalysts comprising a first metal and optionally one or more of a second metal, a third metal or any number of additional metals, optionally on a catalyst support. The first and optional second and third metals may be selected from Group IB, IIB, IIIB, IVB, VB, VIB, VIIB, VIII transition metals, a lanthanide metal, an actinide metal or a metal selected from any of Groups IIIA, IVA, VA, and VIA. Preferred metal combinations for some exemplary catalyst compositions include platinum/tin, platinum/ruthenium, platinum/rhenium, palladium/ruthenium, palladium/rhenium, cobalt/palladium, cobalt/platinum, cobalt/chromium, cobalt/ruthenium, cobalt/tin, silver/palladium, copper/palladium, copper/zinc, nickel/palladium, gold/palladium, ruthenium/rhenium, and ruthenium/iron. Exemplary catalysts are further described in U.S. Pat. No. 7,608,744 and U.S. Pub. No. 2010/0029995, the entireties of which are incorporated herein by reference. In another embodiment, the catalyst comprises a Co/Mo/S catalyst of the type described in U.S. Pub. No. 2009/0069609, the entirety of which is incorporated herein by reference.

In one embodiment, the catalyst comprises a first metal selected from the group consisting of copper, iron, cobalt, nickel, ruthenium, rhodium, palladium, osmium, iridium, platinum, titanium, zinc, chromium, rhenium, molybdenum, and tungsten. Preferably, the first metal is selected from the group consisting of platinum, palladium, cobalt, nickel, and ruthenium. More preferably, the first metal is selected from platinum and palladium. In embodiments of the invention where the first metal comprises platinum, it is preferred that the catalyst comprises platinum in an amount less than 5 wt. %, e.g., less than 3 wt. % or less than 1 wt. %, due to the high commercial demand for platinum.

As indicated above, in some embodiments, the catalyst further comprises a second metal, which typically would function as a promoter. If present, the second metal preferably is selected from the group consisting of copper, molybdenum, tin, chromium, iron, cobalt, vanadium, tungsten, palladium, platinum, lanthanum, cerium, manganese, ruthenium, rhenium, gold, and nickel. More preferably, the second metal is selected from the group consisting of copper, tin, cobalt, rhenium, and nickel. More preferably, the second metal is selected from tin and rhenium.

In certain embodiments where the catalyst includes two or more metals, e.g., a first metal and a second metal, the first metal is present in the catalyst in an amount from 0.1 to 10 wt. %, e.g., from 0.1 to 5 wt. %, or from 0.1 to 3 wt. %. The second metal preferably is present in an amount from 0.1 to 20 wt. %, e.g., from 0.1 to 10 wt. %, or from 0.1 to 5 wt. %. For catalysts comprising two or more metals, the two or more metals may be alloyed with one another or may comprise a non-alloyed metal solution or mixture.

The preferred metal ratios may vary depending on the metals used in the catalyst. In some exemplary embodiments, the mole ratio of the first metal to the second metal is from 10:1 to 1:10, e.g., from 4:1 to 1:4, from 2:1 to 1:2, from 1.5:1 to 1:1.5 or from 1.1:1 to 1:1.1.

The catalyst may also comprise a third metal selected from any of the metals listed above in connection with the first or second metal, so long as the third metal is different from the first and second metals. In preferred aspects, the third metal is selected from the group consisting of cobalt, palladium, ruthenium, copper, zinc, platinum, tin, and rhenium. More preferably, the third metal is selected from cobalt, palladium, and ruthenium. When present, the total weight of the third metal preferably is from 0.05 to 4 wt. %, e.g., from 0.1 to 3 wt. %, or from 0.1 to 2 wt. %.

In addition to one or more metals, in some embodiments of the present invention the catalysts further comprise a support or a modified support. As used herein, the term "modified support" refers to a support that includes a support material and a support modifier, which adjusts the acidity of the support material.

The total weight of the support or modified support, based on the total weight of the catalyst, preferably is from 75 to 99.9 wt. %, e.g., from 78 to 97 wt. %, or from 80 to 95 wt. %. In preferred embodiments that utilize a modified support, the support modifier is present in an amount from 0.1 to 50 wt. %, e.g., from 0.2 to 25 wt. %, from 0.5 to 15 wt. %, or from 1 to 8 wt. %, based on the total weight of the catalyst. The metals of the catalysts may be dispersed throughout the support, layered throughout the support, coated on the outer surface of the support (i.e., egg shell), or decorated on the surface of the support.

As will be appreciated by those of ordinary skill in the art, support materials are selected such that the catalyst system is suitably active, selective and robust under the process conditions employed for the formation of ethanol.

Suitable support materials may include, for example, stable metal oxide-based supports or ceramic-based supports. Preferred supports include silicaceous supports, such as silica, silica/alumina, a Group IIA silicate such as calcium metasilicate, pyrogenic silica, high purity silica, and mixtures thereof. Other supports may include, but are not limited to, iron oxide, alumina, titania, zirconia, magnesium oxide, carbon, graphite, high surface area graphitized carbon, activated carbons, and mixtures thereof.

As indicated, the catalyst support may be modified with a support modifier. In some embodiments, the support modifier may be an acidic modifier that increases the acidity of the catalyst. Suitable acidic support modifiers may be selected from the group consisting of: oxides of Group IVB metals, oxides of Group VB metals, oxides of Group VIB metals, oxides of Group VIIB metals, oxides of Group VIIIB metals, aluminum oxides, and mixtures thereof. Acidic support modifiers include those selected from the group consisting of $TiO_2$, $ZrO_2$, $Nb_2O_5$, $Ta_2O_5$, $Al_2O_3$, $B_2O_3$, $P_2O_5$, and $Sb_2O_3$. Preferred acidic support modifiers include those selected from the group consisting of $TiO_2$, $ZrO_2$, $Nb_2O_5$, $Ta_2O_5$, and $Al_2O_3$. The acidic modifier may also include selected from the group consisting of $WO_3$, $MoO_3$, $Fe_2O_3$, $Cr_2O_3$, $V_2O_5$, $MnO_2$, $CuO$, $Co_2O_3$, and $Bi_2O_3$.

In another embodiment, the support modifier may be a basic modifier that has a low volatility or no volatility. Such basic modifiers, for example, may be selected from the group consisting of: (i) alkaline earth metal oxides, (ii) alkali metal oxides, (iii) alkaline earth metal metasilicates, (iv) alkali metal metasilicates, (v) Group IIB metal oxides, (vi) Group IIB metal metasilicates, (vii) Group IIIB metal oxides, (viii) Group IIIB metal metasilicates, and mixtures thereof. In addition to oxides and metasilicates, other types of modifiers including nitrates, nitrites, acetates, and lactates may be used. Preferably, the support modifier is selected from the group consisting of oxides and metasilicates of any of sodium, potassium, magnesium, calcium, scandium, yttrium, and zinc, as well as mixtures of any of the foregoing. More preferably, the basic support modifier is a calcium silicate, and even more preferably calcium metasilicate ($CaSiO_3$). If the basic support modifier comprises calcium metasilicate, it is preferred that at least a portion of the calcium metasilicate is in crystalline form.

A preferred silica support material is SS61138 High Surface Area (HSA) Silica Catalyst Carrier from Saint-Gobain NorPro. The Saint-Gobain NorPro SS61138 silica exhibits the following properties: contains approximately 95 wt. % high surface area silica; surface area of about 250 $m^2$/g; median pore diameter of about 12 nm; average pore volume of about 1.0 $cm^3$/g as measured by mercury intrusion porosimetry and a packing density of about 0.352 $g/cm^3$ (22 $lb/ft^3$).

A preferred silica/alumina support material is KA-160 silica spheres from Sud Chemie having a nominal diameter of about 5 mm, a density of about 0.562 g/ml, an absorptivity of about 0.583 g $H_2O$/g support, a surface area of about 160 to 175 $m^2$/g, and a pore volume of about 0.68 ml/g.

The catalyst compositions suitable for use with the present invention preferably are formed through metal impregnation of the modified support, although other processes such as chemical vapor deposition may also be employed. Such impregnation techniques are described in U.S. Pat. Nos. 7,608,744 and 7,863,489 and U.S. Pub. No. 2010/0197485 referred to above, the entireties of which are incorporated herein by reference.

For purposes of the present invention, the term "conversion" refers to the amount of acetic acid in the feed that is converted to a compound other than acetic acid. Conversion is expressed as a mole percentage based on acetic acid in the feed. The conversion may be at least 10%, e.g., at least 20%, at least 40%, at least 50%, at least 60%, at least 70% or at least 80%. Although catalysts that have high conversions are desirable, such as at least 80% or at least 90%, in some embodiments a low conversion may be acceptable at high selectivity for ethanol. It is, of course, well understood that in many cases, it is possible to compensate for conversion by appropriate recycle streams or use of larger reactors, but it is more difficult to compensate for poor selectivity.

Selectivity is expressed as a mole percent based on converted acetic acid. It should be understood that each compound converted from acetic acid has an independent selectivity and that selectivity is independent from conversion. For example, if 60 mole % of the converted acetic acid is converted to ethanol, we refer to the ethanol selectivity as 60%. Preferably, the catalyst selectivity to ethoxylates is at least 60%, e.g., at least 70%, or at least 80%. As used herein, the term "ethoxylates" refers specifically to the compounds ethanol, acetaldehyde, and ethyl acetate. Preferably, the selectivity to ethanol in the first reaction zone is at least 80%, e.g., at least 85% or at least 88%. Preferred embodiments of the hydrogenation process also have low selectivity to undesirable products, such as methane, ethane, and carbon dioxide. The selectivity to these undesirable products preferably is less than 4%, e.g., less than 2% or less than 1%. More preferably, these undesirable products are present in undetectable amounts. Formation of alkanes may be low, and ideally less than 2%, less than 1%, or less than 0.5% of the acetic acid passed over the catalyst is converted to alkanes, which have little value other than as fuel.

The term "productivity," as used herein, refers to the grams of a specified product, e.g., ethanol, formed during the hydrogenation based on the kilograms of catalyst used per hour. A productivity of at least 100 grams of ethanol per kilogram of catalyst per hour, e.g., at least 400 grams of ethanol per kilogram of catalyst per hour or at least 600 grams of ethanol per kilogram of catalyst per hour, is preferred. In terms of ranges, the productivity preferably is from 100 to 3,000 grams of ethanol per kilogram of catalyst per hour, e.g., from 400 to 2,500 grams of ethanol per kilogram of catalyst per hour or from 600 to 2,000 grams of ethanol per kilogram of catalyst per hour.

Operating under the conditions of the present invention may result in ethanol production on the order of at least 0.1 tons of ethanol per hour, e.g., at least 1 ton of ethanol per hour, at least 5 tons of ethanol per hour, or at least 10 tons of ethanol per hour. Larger scale industrial production of ethanol, depending on the scale, generally should be at least 1 ton of ethanol per hour, e.g., at least 15 tons of ethanol per hour or at least 30 tons of ethanol per hour. In terms of ranges, for large scale industrial production of ethanol, the process of the present invention may produce from 0.1 to 160 tons of ethanol per hour, e.g., from 15 to 160 tons of ethanol per hour or from 30 to 80 tons of ethanol per hour. Ethanol production from fermentation, due the economies of scale, typically does not permit the single facility ethanol production that may be achievable by employing embodiments of the present invention.

In various embodiments of the present invention, the crude ethanol product produced by the reactor, before any subsequent processing, such as purification and separation, will typically comprise acetic acid, ethanol and water. As used herein, the term "crude ethanol product" refers to any composition comprising from 5 to 70 wt. % ethanol and from 5 to 40 wt. % water. Preferably, vinyl acetate in the crude vinyl acetate feed may be reacted such that no detectable amounts of vinyl acetate are present in the crude ethanol composition. Exemplary compositional ranges for the crude ethanol product are provided in Table 1. The "others" identified in Table 1 may include, for example, esters, ethers, aldehydes, ketones, alkanes, and carbon dioxide.

TABLE 1

CRUDE ETHANOL PRODUCT COMPOSITIONS

| Component | Conc. (wt. %) | Conc. (wt. %) | Conc. (wt. %) | Conc. (wt. %) |
|---|---|---|---|---|
| Ethanol | 5 to 70 | 15 to 70 | 15 to 50 | 25 to 50 |
| Acetic Acid | 0 to 90 | 0 to 50 | 5 to 70 | 5 to 50 |
| Water | 5 to 30 | 5 to 28 | 10 to 26 | 10 to 22 |
| Ethyl Acetate | 0 to 30 | 0 to 20 | 1 to 12 | 3 to 10 |
| Acetaldehyde | 0 to 10 | 0 to 3 | 0.1 to 3 | 0.2 to 2 |
| Others | 0.1 to 10 | 0.1 to 6 | 0.1 to 4 | — |

In one embodiment, the crude ethanol product may comprise acetic acid in an amount less than 20 wt. %, e.g., of less than 15 wt. %, less than 10 wt. % or less than 5 wt. %. In embodiments having lower amounts of acetic acid, the conversion of acetic acid is preferably greater than 75%, e.g., greater than 85% or greater than 90%. In addition, the selectivity to ethanol may also be preferably high, and is greater than 75%, e.g., greater than 85% or greater than 90%.

Ethanol Recovery

Figure 3:
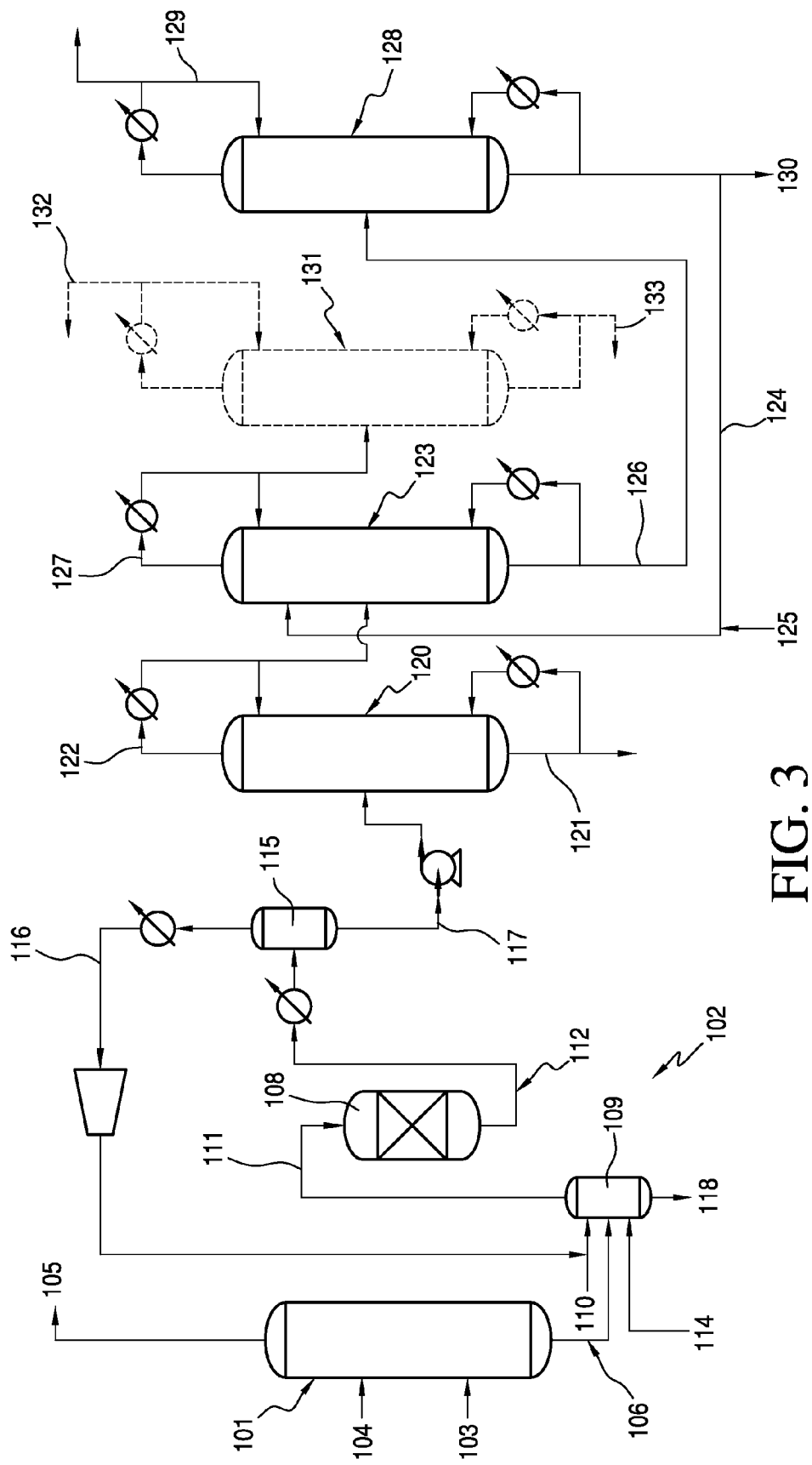
FIG. 3 is a schematic diagram of an ethanol separation process having four columns in accordance with an embodiment of the present invention.
Figure 4:
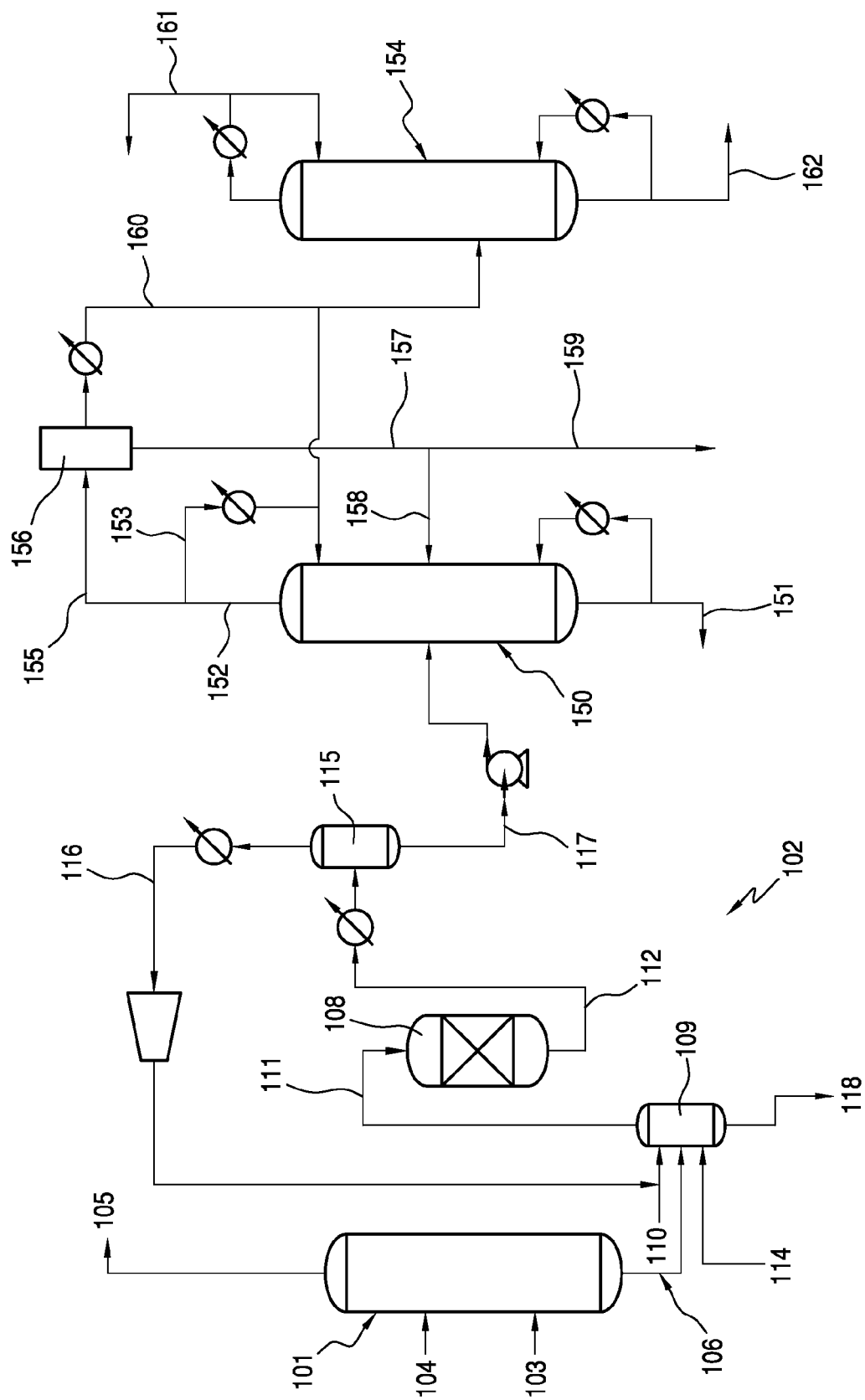
FIG. 4 is a schematic diagram of another ethanol separation process having two columns with an intervening water separation in accordance with an embodiment of the present invention.
Figure 5:
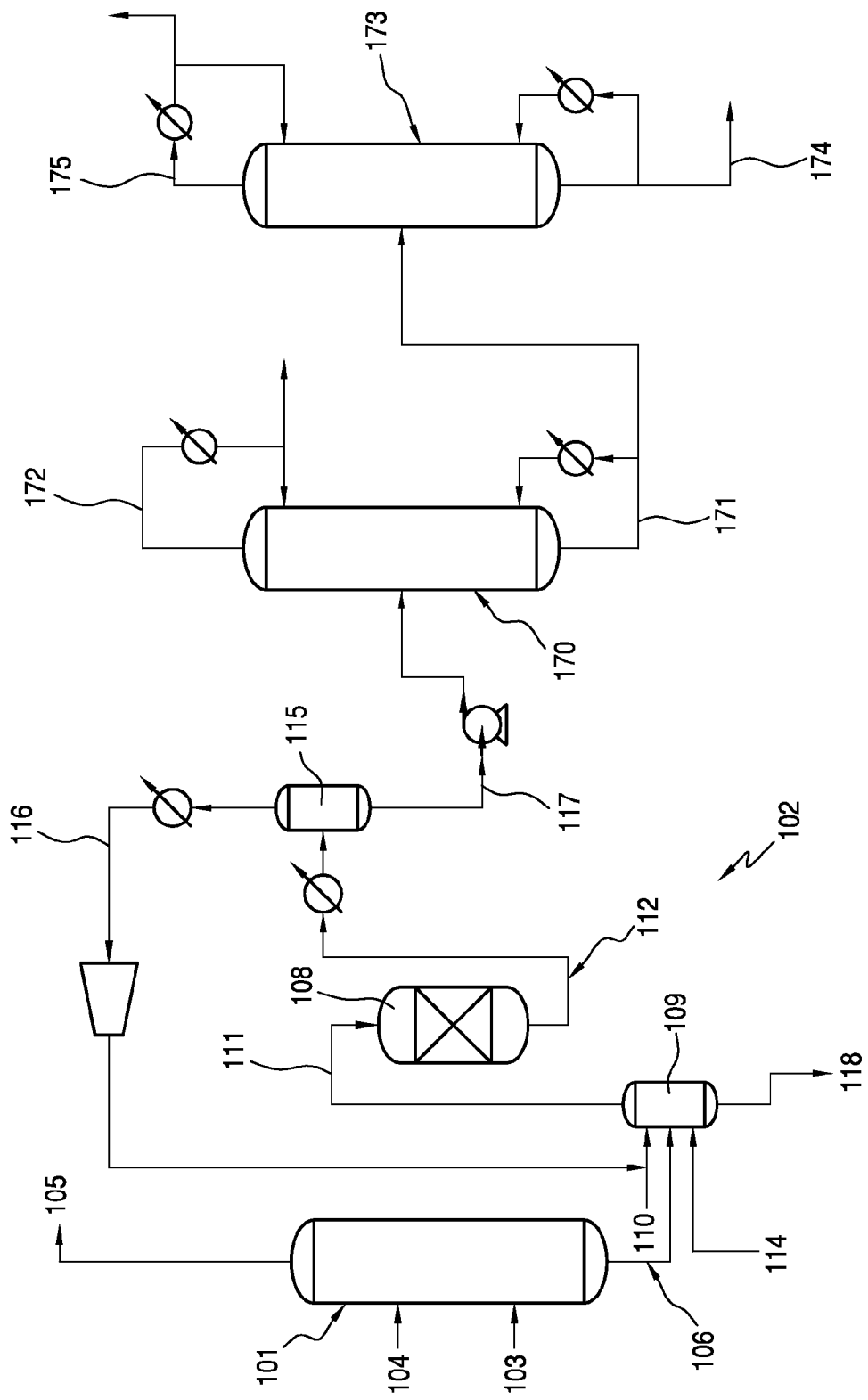
FIG. 5 is a schematic diagram of another hydrogenation process having two columns in accordance with an embodiment of the present invention.

Returning to FIGS. 1A, 1B, 2A, and 2B, a liquid stream 117 is produced from reaction zone 102. Ethanol may be recovered from the liquid stream 117 using several different separation processes. FIGS. 3, 4, and 5, illustrate exemplary ethanol separation processes. For purposes of convenience, FIG. 1B is shown with each of these exemplary processes, but it understood that any of FIGS. 1A, 1B 2A, and 2B may be combined with the ethanol separation processes shown in FIGS. 3, 4, and 5.

In one embodiment, the contents of liquid stream 117 are substantially similar to the reaction mixture obtained from the reaction zone, except that the composition has been depleted of hydrogen, carbon dioxide, methane and/or ethane, which are removed by separator 115. Liquid stream 117 may also be referred to as a crude ethanol product. Exemplary components of liquid stream 117 are provided in Table 2. It should be understood that liquid stream 117 may contain other components, not listed in Table 2.

TABLE 2

COLUMN FEED COMPOSITION
(Liquid Stream 117)

|  | Conc. (wt. %) | Conc. (wt. %) | Conc. (wt. %) |
|---|---|---|---|
| Ethanol | 5 to 70 | 10 to 60 | 15 to 50 |
| Acetic Acid | <90 | 5 to 80 | 5 to 70 |
| Water | 5 to 30 | 5 to 28 | 10 to 26 |
| Ethyl Acetate | <30 | 0.001 to 20 | 1 to 12 |
| Acetaldehyde | <10 | 0.001 to 3 | 0.1 to 3 |
| Acetals | <5 | 0.001 to 2 | 0.005 to 1 |
| Acetone | <5 | 0.0005 to 0.05 | 0.001 to 0.03 |
| Other Esters | <5 | <0.005 | <0.001 |
| Other Ethers | <5 | <0.005 | <0.001 |
| Other Alcohols | <5 | <0.005 | <0.001 |

The amounts indicated as less than (<) in the tables throughout the present specification are preferably not present and if present may be present in trace amounts or in amounts greater than 0.0001 wt. %.

The "other esters" in Table 2 may include, but are not limited to, ethyl propionate, methyl acetate, isopropyl acetate, n-propyl acetate, n-butyl acetate or mixtures thereof. The "other ethers" in Table 2 may include, but are not limited to, diethyl ether, methyl ethyl ether, isobutyl ethyl ether or mixtures thereof. The "other alcohols" in Table 2 may include, but are not limited to, methanol, isopropanol, n-propanol, n-butanol or mixtures thereof. In one embodiment, the liquid stream 117 may comprise propanol, e.g., isopropanol and/or n-propanol, in an amount from 0.001 to 0.1 wt. %, from 0.001 to 0.05 wt. % or from 0.001 to 0.03 wt. %. In should be understood that these other components may be carried through in any of the distillate or residue streams described herein and will not be further described herein, unless indicated otherwise.

Optionally, the crude ethanol product in line 112 or liquid stream 117 may be further fed to an esterification reactor, hydrogenolysis reactor, or combination thereof. An esterification reactor may be used to consume residual acetic acid present in the crude ethanol product to further reduce the amount of acetic acid that would otherwise need to be removed. Hydrogenolysis may be used to convert ethyl acetate in the crude ethanol product to ethanol.

In the embodiment shown in FIG. 3, liquid stream 117 is introduced in the lower part of first column 120, e.g., lower half or lower third. In first column 120, also referred to as an acid separation column, removes acetic acid, a portion of the water, and other heavy components, if present, from the feed, preferably continuously, as residue, 121. Some or all of the residue may be returned and/or recycled back to reaction zone 102 via line 121. Recycling the acetic acid in line 121 to the vaporizer 109 may reduce the amount of heavies that need to be purged from vaporizer 109. Reducing the amount of heavies to be purged may improve efficiencies of the process while reducing byproducts.

First column 120 also forms an overhead distillate, which is withdrawn in line 122, and which may be condensed and refluxed, for example, at a ratio from 10:1 to 1:10, e.g., from 3:1 to 1:3 or from 1:2 to 2:1.

When column 120 is operated under standard atmospheric pressure, the temperature of the residue exiting in line 121 preferably is from 95° C. to 120° C., e.g., from 110° C. to 117° C. or from 111° C. to 115° C. The temperature of the distillate exiting in line 122 preferably is from 70° C. to 110° C., e.g., from 75° C. to 95° C. or from 80° C. to 90° C. Column 120 preferably operates at ambient pressure. In other embodiments, the pressure of first column 120 may range from 0.1 kPa to 510 kPa, e.g., from 1 kPa to 475 kPa or from 1 kPa to 375 kPa. Exemplary components of the distillate and residue compositions for first column 120 are provided in Table 3 below. It should also be understood that the distillate and residue may also contain other components, not listed, such as components in the feed. For convenience, the distillate and residue of the first column may also be referred to as the "first distillate" or "first residue." The distillates or residues of the other columns may also be referred to with similar numeric modifiers (second, third, etc.) in order to distinguish them from one another, but such modifiers should not be construed as requiring any particular separation order.

TABLE 3

| ACID COLUMN 120 (FIG. 3) | | | |
|---|---|---|---|
| | Conc. (wt. %) | Conc. (wt. %) | Conc. (wt. %) |
| Distillate | | | |
| Ethanol | 20 to 75 | 30 to 70 | 40 to 65 |
| Water | 10 to 40 | 15 to 35 | 20 to 35 |
| Acetic Acid | <2 | 0.001 to 0.5 | 0.01 to 0.2 |
| Ethyl Acetate | <60 | 5.0 to 40 | 10 to 30 |
| Acetaldehyde | <10 | 0.001 to 5 | 0.01 to 4 |

TABLE 3-continued

| ACID COLUMN 120 (FIG. 3) | | | |
|---|---|---|---|
| | Conc. (wt. %) | Conc. (wt. %) | Conc. (wt. %) |
| Acetal | <0.1 | <0.1 | <0.05 |
| Acetone | <0.05 | 0.001 to 0.03 | 0.01 to 0.025 |
| Residue | | | |
| Acetic Acid | 60 to 100 | 70 to 95 | 85 to 92 |
| Water | <30 | 1 to 20 | 1 to 15 |
| Ethanol | <1 | <0.9 | <0.07 |

As shown in Table 3, without being bound by theory, it has surprisingly and unexpectedly been discovered that when any amount of acetal is detected in the feed that is introduced to the acid separation column 120, the acetal appears to decompose in the column such that less or even no detectable amounts are present in the distillate and/or residue.

The distillate in line 122 preferably comprises ethanol, ethyl acetate, and water, along with other impurities, which may be difficult to separate due to the formation of binary and tertiary azeotropes. To further separate distillate, line 122 is introduced to the second column 123, also referred to as the "light ends column," preferably in the middle part of column 123, e.g., middle half or middle third. Preferably the second column 123 is an extractive distillation column, and an extraction agent is added thereto via lines 124 and/or 125. Extractive distillation is a method of separating close boiling components, such as azeotropes, by distilling the feed in the presence of an extraction agent. The extraction agent preferably has a boiling point that is higher than the compounds being separated in the feed. In preferred embodiments, the extraction agent is comprised primarily of water. As indicated above, the first distillate in line 122 that is fed to the second column 123 comprises ethyl acetate, ethanol, and water. These compounds tend to form binary and ternary azeotropes, which decrease separation efficiency. As shown, in one embodiment the extraction agent comprises the third residue in line 124. Preferably, the recycled third residue in line 124 is fed to second column 123 at a point higher than the first distillate in line 122. In one embodiment, the recycled third residue in line 124 is fed near the top of second column 123 or fed, for example, above the feed in line 122 and below the reflux line from the condensed overheads. In a tray column, the third residue in line 124 is continuously added near the top of the second column 123 so that an appreciable amount of the third residue is present in the liquid phase on all of the trays below. In another embodiment, the extraction agent is fed from a source outside of the process via line 125 to second column 123. Preferably this extraction agent comprises water.

The molar ratio of the water in the extraction agent to the ethanol in the feed to the second column is preferably at least 0.5:1, e.g., at least 1:1 or at least 3:1. In terms of ranges, preferred molar ratios may range from 0.5:1 to 8:1, e.g., from 1:1 to 7:1 or from 2:1 to 6.5:1. Higher molar ratios may be used but with diminishing returns in terms of the additional ethyl acetate in the second distillate and decreased ethanol concentrations in the second column distillate.

In one embodiment, an additional extraction agent, such as water from an external source, dimethylsulfoxide, glycerine, diethylene glycol, 1-naphthol, hydroquinone, N,N'-dimethylformamide, 1,4-butanediol; ethylene glycol-1,5-pentanediol; propylene glycol-tetraethylene glycol-polyethylene glycol; glycerine-propylene glycol-tetraethylene glycol-1,4-butanediol, ethyl ether, methyl formate, cyclohexane, N,N'- dimethyl-1,3-propanediamine, N,N'-dimethylethylenediamine, diethylene triamine, hexamethylene diamine and 1,3-diaminopentane, an alkylated thiopene, dodecane, tridecane, tetradecane and chlorinated paraffins, may be added to second column 123. Some suitable extraction agents include those described in U.S. Pat. Nos. 4,379,028, 4,569,726, 5,993,610 and 6,375,807, the entire contents and disclosure of which are hereby incorporated by reference. The additional extraction agent may be combined with the recycled third residue in line 124 and co-fed to the second column 123. The additional extraction agent may also be added separately to the second column 123. In one aspect, the extraction agent comprises an extraction agent, e.g., water, derived from an external source via line 125 and none of the extraction agent is derived from the third residue.

Second column 123 may be a tray or packed column. In one embodiment, second column 123 is a tray column having from 5 to 70 trays, e.g., from 15 to 50 trays or from 20 to 45 trays. Although the temperature and pressure of second column 123 may vary, when at atmospheric pressure the temperature of the second residue exiting in line 126 preferably is from 60° C. to 90° C., e.g., from 70° C. to 90° C. or from 80° C. to 90° C. The temperature of the second distillate exiting in line 127 from second column 123 preferably is from 50° C. to 90° C., e.g., from 60° C. to 80° C. or from 60° C. to 70° C. Column 123 may operate at atmospheric pressure. In other embodiments, the pressure of second column 123 may range from 0.1 kPa to 510 kPa, e.g., from 1 kPa to 475 kPa or from 1 kPa to 375 kPa. Exemplary components for the distillate and residue compositions for second column 123 are provided in Table 4 below. It should be understood that the distillate and residue may also contain other components, not listed, such as components in the feed.

TABLE 4

SECOND COLUMN 123 (FIG. 3)

|  | Conc. (wt. %) | Conc. (wt. %) | Conc. (wt. %) |
|---|---|---|---|
| Distillate |  |  |  |
| Ethyl Acetate | 10 to 99 | 25 to 95 | 50 to 93 |
| Acetaldehyde | <25 | 0.5 to 15 | 1 to 8 |
| Water | <25 | 0.5 to 20 | 4 to 16 |
| Ethanol | <30 | 0.001 to 15 | 0.01 to 5 |
| Acetal | <5 | 0.001 to 2 | 0.01 to 1 |
| Residue |  |  |  |
| Water | 30 to 90 | 40 to 85 | 50 to 85 |
| Ethanol | 10 to 75 | 15 to 60 | 20 to 50 |
| Ethyl Acetate | <3 | 0.001 to 2 | 0.001 to 0.5 |
| Acetic Acid | <0.5 | 0.001 to 0.3 | 0.001 to 0.2 |

In preferred embodiments, the recycling of the third residue promotes the separation of ethyl acetate from the residue of the second column 123. For example, the weight ratio of ethyl acetate in the second residue to second distillate preferably is less than 0.4:1, e.g., less than 0.2:1 or less than 0.1:1. In embodiments that use an extractive distillation column with water as an extraction agent as the second column 123, the weight ratio of ethyl acetate in the second residue to ethyl acetate in the second distillate approaches zero.

The weight ratio of ethanol in the second residue to second distillate preferably is at least 3:1, e.g., at least 6:1, at least 8:1, at least 10:1 or at least 15:1. All or a portion of the third residue is recycled to the second column. In one embodiment, all of the third residue may be recycled until process reaches a steady state and then a portion of the third residue is recycled with the remaining portion being purged from the system. The composition of the second residue will tend to have lower amounts of ethanol than when the third residue is not recycled. As the third residue is recycled, the composition of the second residue, as provided in Table 4, comprises less than 30 wt. % of ethanol, e.g., less than 20 wt. % or less than 15 wt. %. The majority of the second residue preferably comprises water. Notwithstanding this effect, the extractive distillation step advantageously also reduces the amount of ethyl acetate that is sent to the third column, which is highly beneficial in ultimately forming a highly pure ethanol product.

As shown, the second residue from second column 123, which comprises ethanol and water, is fed via line 126 to third column 128, also referred to as the "product column." More preferably, the second residue in line 126 is introduced in the lower part of third column 128, e.g., lower half or lower third. Third column 128 recovers ethanol, which preferably is substantially pure with respect to organic impurities and other than the azeotropic water content, as the distillate in line 129. The distillate of third column 128 preferably is refluxed as shown in FIG. 3, for example, at a reflux ratio from 1:10 to 10:1, e.g., from 1:3 to 3:1 or from 1:2 to 2:1. The third residue in line 124, which comprises primarily water, preferably is returned to the second column 123 as an extraction agent as described above. In one embodiment, a first portion of the third residue in line 124 is recycled to the second column and a second portion is purged and removed from the system via line 130. In one embodiment, once the process reaches steady state, the second portion of water to be purged is substantially similar to the amount water formed in the hydrogenation of acetic acid. In one embodiment, a portion of the third residue may be used to hydrolyze any other stream, such as one or more streams comprising ethyl acetate.

Although FIG. 3 shows third residue being directly recycled to second column 123, third residue may also be returned indirectly, for example, by storing a portion or all of the third residue in a tank (not shown) or treating the third residue to further separate any minor components such as aldehydes, higher molecular weight alcohols, or esters in one or more additional columns (not shown).

Third column 128 is preferably a tray column as described above and operates at atmospheric pressure or optionally at pressures above or below atmospheric pressure. The temperature of the third distillate exiting in line 129 preferably is from 60° C. to 110° C., e.g., from 70° C. to 100° C. or from 75° C. to 95° C. The temperature of the third residue in line 124 preferably is from 70° C. to 115° C., e.g., from 80° C. to 110° C. or from 85° C. to 105° C. Exemplary components of the distillate and residue compositions for third column 128 are provided in Table 5 below. It should be understood that the distillate and residue may also contain other components, not listed, such as components in the feed.

TABLE 5

THIRD COLUMN 128 (FIG. 3)

|  | Conc. (wt. %) | Conc. (wt. %) | Conc. (wt. %) |
|---|---|---|---|
| Distillate |  |  |  |
| Ethanol | 75 to 96 | 80 to 96 | 85 to 96 |
| Water | <12 | 1 to 9 | 3 to 8 |
| Acetic Acid | <12 | 0.0001 to 0.1 | 0.005 to 0.05 |
| Ethyl Acetate | <12 | 0.0001 to 0.05 | 0.005 to 0.025 |
| Acetaldehyde | <12 | 0.0001 to 0.1 | 0.005 to 0.05 |
| Diethyl Acetal | <12 | 0.0001 to 0.05 | 0.005 to 0.025 |
| Residue |  |  |  |
| Water | 75 to 100 | 80 to 100 | 90 to 100 |
| Ethanol | <0.8 | 0.001 to 0.5 | 0.005 to 0.05 |

TABLE 5-continued

| THIRD COLUMN 128 (FIG. 3) | | | |
|---|---|---|---|
| | Conc. (wt. %) | Conc. (wt. %) | Conc. (wt. %) |
| Ethyl Acetate | <1 | 0.001 to 0.5 | 0.005 to 0.2 |
| Acetic Acid | <2 | 0.001 to 0.5 | 0.005 to 0.2 |

In one embodiment, the third residue in line 124 is withdrawn from third column 128 at a temperature higher than the operating temperature of the second column 123. Preferably, the third residue in line 124 is integrated to heat one or more other streams or is reboiled prior to be returned to the second column 123.

Any of the compounds that are carried through the distillation process from the feed or crude reaction product generally remain in the third distillate in amounts of less 0.1 wt. %, based on the total weight of the third distillate composition, e.g., less than 0.05 wt. % or less than 0.02 wt. %. In one embodiment, one or more sidestreams may remove impurities from any of the columns in the system. Preferably at least one sidestream is used to remove impurities from the third column 128. The impurities may be purged and/or retained within the system.

The third distillate in line 129 may be further purified to form an anhydrous ethanol product stream, i.e., "finished anhydrous ethanol," using one or more additional separation systems, such as, for example, distillation columns, adsorption units, membranes, or molecular sieves. Suitable adsorption units include pressure swing adsorption units and thermal swing adsorption unit.

Returning to second column 123, the second distillate preferably is refluxed as shown in FIG. 3, optionally at a reflux ratio of 1:10 to 10:1, e.g., from 1:5 to 5:1 or from 1:3 to 3:1. The second distillate in line 127 may be purged or recycled to the reaction zone. In an optional embodiment, the second distillate in line 127 may be further processed in an optional fourth column 131, also referred to as the "acetaldehyde removal column." Whether optional fourth column 131 is required depends primarily on the acetaldehyde concentration in line 127. In fourth column 131 the second distillate is separated into a fourth distillate, which comprises acetaldehyde, in line 132 and a fourth residue, which comprises ethyl acetate, in line 133. The fourth distillate preferably is refluxed at a reflux ratio from 1:20 to 20:1, e.g., from 1:15 to 15:1 or from 1:10 to 10:1, and a portion of the fourth distillate is returned to the reaction zone 102. For example, the fourth distillate may be combined with the acetic acid feed, added to the vaporizer 109, or added directly to the reactor 108. The fourth distillate preferably is co-fed with the acetic acid in feed line 114 or optional line 113 to vaporizer 109. Without being bound by theory, since acetaldehyde may be hydrogenated to form ethanol, the recycling of a stream that contains acetaldehyde to the reaction zone increases the yield of ethanol and decreases byproduct and waste generation. In another embodiment, the acetaldehyde may be collected and utilized, with or without further purification, to make useful products including but not limited to n-butanol, 1,3-butanediol, and/or crotonaldehyde and derivatives.

The fourth residue of fourth column 131 may be purged via line 133. The fourth residue primarily comprises ethyl acetate and ethanol, which may be suitable for use as a solvent mixture or in the production of esters. In one preferred embodiment, the acetaldehyde is removed from the second distillate in fourth column 131 such that no detectable amount of acetaldehyde is present in the residue of column 131.

Fourth column 131 is preferably a tray column as described above and preferably operates above atmospheric pressure. In one embodiment, the pressure is from 120 kPa to 5,000 kPa, e.g., from 200 kPa to 4,500 kPa, or from 400 kPa to 3,000 kPa. In a preferred embodiment the fourth column 131 may operate at a pressure that is higher than the pressure of the other columns.

The temperature of the fourth distillate exiting in line 132 preferably is from 60° C. to 110° C., e.g., from 70° C. to 100° C. or from 75° C. to 95° C. The temperature of the residue in line 133 preferably is from 70° C. to 115° C., e.g., from 80° C. to 110° C. or from 85° C. to 110° C. Exemplary components of the distillate and residue compositions for fourth column 131 are provided in Table 6 below. It should be understood that the distillate and residue may also contain other components, not listed, such as components in the feed.

TABLE 6

| OPTIONAL FOURTH COLUMN 131 (FIG. 3) | | | |
|---|---|---|---|
| | Conc. (wt. %) | Conc. (wt. %) | Conc. (wt. %) |
| Distillate | | | |
| Acetaldehyde | 2 to 80 | 2 to 50 | 5 to 40 |
| Ethyl Acetate | <90 | 30 to 80 | 40 to 75 |
| Ethanol | <30 | 0.001 to 25 | 0.01 to 20 |
| Water | <25 | 0.001 to 20 | 0.01 to 15 |
| Residue | | | |
| Ethyl Acetate | 40 to 100 | 50 to 100 | 60 to 100 |
| Ethanol | <40 | 0.001 to 30 | 0.01 to 15 |
| Water | <25 | 0.001 to 20 | 2 to 15 |
| Acetaldehyde | <1 | 0.001 to 0.5 | Not detectable |
| Acetal | <3 | 0.001 to 2 | 0.01 to 1 |

In one embodiment, a portion of the third residue in line 124 is recycled to second column 123. In one embodiment, recycling the third residue further reduces the aldehyde components in the second residue and concentrates these aldehyde components in second distillate in line 127 and thereby sent to the fourth column 131, wherein the aldehydes may be more easily separated. The third distillate, e.g. intermediate stream, in line 129 may have lower concentrations of aldehydes and esters due to the recycling of third residue in line 124.

FIG. 4 illustrates another exemplary separation system used to produce ethanol from liquid stream 117. Liquid stream 117 is introduced in the middle or lower portion of a first column 150, also referred to as acid-water column. For purposes of convenience, the columns in each exemplary separation process, may be referred as the first, second, third, etc., columns, but it is understood that first column 150 in FIG. 4 operates differently than the first column 120 of FIG. 3. In one embodiment, no entrainers are added to first column 150. In FIG. 4, first column 150, water and unreacted acetic acid, along with any other heavy components, if present, are removed from liquid stream 117 and are withdrawn, preferably continuously, as a first residue in line 151. Preferably, a substantial portion of the water in the crude ethanol product that is fed to first column 150 may be removed in the first residue, for example, up to about 90% of the water from the crude ethanol product, and more preferably up to about 75%. First column 150 also forms a first distillate, which is withdrawn in line 152.

When column 150 is operated under about 170 kPa, the temperature of the residue exiting in line 151 preferably is from 90° C. to 130° C., e.g., from 95° C. to 120° C. or from 100° C. to 115° C. The temperature of the distillate exiting in line 152 preferably is from 60° C. to 90° C., e.g., from 65° C. to 85° C. or from 70° C. to 80° C. In some embodiments, the pressure of first column 150 may range from 0.1 kPa to 510 kPa, e.g., from 1 kPa to 475 kPa or from 1 kPa to 375 kPa.

The first distillate in line 152 comprises water, in addition to ethanol and other organics. In terms of ranges, the concentration of water in the first distillate in line 152 preferably is from 4 wt. % to 38 wt. %, e.g., from 7 wt. % to 32 wt. %, or from 7 to 25 wt. %. A portion of first distillate in line 153 may be condensed and refluxed, for example, at a ratio from 10:1 to 1:10, e.g., from 3:1 to 1:3 or from 1:2 to 2:1. It is understood that reflux ratios may vary with the number of stages, feed locations, column efficiency and/or feed composition. Operating with a reflux ratio of greater than 3:1 may be less preferred because more energy may be required to operate the first column 150. The condensed portion of the first distillate may also be fed to a second column 154.

The remaining portion of the first distillate in 155 is fed to a water separation unit 156. Water separation unit 156 may be an adsorption unit, membrane, molecular sieves, extractive column distillation, or a combination thereof. A membrane or an array of membranes may also be employed to separate water from the distillate. The membrane or array of membranes may be selected from any suitable membrane that is capable of removing a permeate water stream from a stream that also comprises ethanol and ethyl acetate.

In a preferred embodiment, water separation unit 156 is a pressure swing adsorption (PSA) unit. The PSA unit is optionally operated at a temperature from 30° C. to 160° C., e.g., from 80° C. to 140° C., and a pressure from 0.01 kPa to 550 kPa, e.g., from 1 kPa to 150 kPa. The PSA unit may comprise two to five beds. Water separation unit 156 may remove at least 95% of the water from the portion of first distillate in line 155, and more preferably from 99% to 99.99% of the water from the first distillate, in a water stream 157. All or a portion of water stream 157 may be returned to column 150 in line 158, where the water preferably is ultimately recovered from column 150 in the first residue in line 151. Additionally or alternatively, all or a portion of water stream 157 may be purged via line 159. The remaining portion of first distillate exits the water separation unit 156 as ethanol mixture stream 160. Ethanol mixture stream 160 may have a low concentration of water of less than 10 wt. %, e.g., less than 6 wt. % or less than 2 wt. %. Exemplary components of ethanol mixture stream 160 and first residue in line 151 are provided in Table 7 below. It should also be understood that these streams may also contain other components, not listed, such as components derived from the feed.

TABLE 7

FIRST COLUMN 150 WITH PSA (FIG. 4)

|  | Conc. (wt. %) | Conc. (wt. %) | Conc. (wt. %) |
|---|---|---|---|
| Ethanol Mixture Stream |  |  |  |
| Ethanol | 20 to 95 | 30 to 95 | 40 to 95 |
| Water | <10 | 0.01 to 6 | 0.1 to 2 |
| Acetic Acid | <2 | 0.001 to 0.5 | 0.01 to 0.2 |
| Ethyl Acetate | <60 | 1 to 55 | 5 to 55 |
| Acetaldehyde | <10 | 0.001 to 5 | 0.01 to 4 |
| Acetal | <0.1 | <0.1 | <0.05 |
| Acetone | <0.05 | 0.001 to 0.03 | 0.01 to 0.025 |
| Residue |  |  |  |
| Acetic Acid | <90 | 1 to 50 | 2 to 35 |
| Water | 30 to 100 | 45 to 95 | 60 to 90 |
| Ethanol | <1 | <0.9 | <0.3 |

Preferably, ethanol mixture stream 160 is not returned or refluxed to first column 150. The condensed portion of the first distillate in line 153 may be combined with ethanol mixture stream 160 to control the water concentration fed to the second column 154. For example, in some embodiments the first distillate may be split into equal portions, while in other embodiments, all of the first distillate may be condensed or all of the first distillate may be processed in the water separation unit. In FIG. 4, the condensed portion in line 153 and ethanol mixture stream 160 are co-fed to second column 154. In other embodiments, the condensed portion in line 153 and ethanol mixture stream 160 may be separately fed to second column 154. The combined distillate and ethanol mixture has a total water concentration of greater than 0.5 wt. %, e.g., greater than 2 wt. % or greater than 5 wt. %. In terms of ranges, the total water concentration of the combined distillate and ethanol mixture may be from 0.5 to 15 wt. %, e.g., from 2 to 12 wt. %, or from 5 to 10 wt. %.

The second column 154 in FIG. 4, also referred to as the "light ends column," removes ethyl acetate and acetaldehyde from the first distillate in line 153 and/or ethanol mixture stream 160. Ethyl acetate and acetaldehyde are removed as a second distillate in line 161 and ethanol is removed as the second residue in line 162. Second column 154 may be a tray column or packed column. In one embodiment, second column 154 is a tray column having from 5 to 70 trays, e.g., from 15 to 50 trays or from 20 to 45 trays.

Second column 154 operates at a pressure ranging from 0.1 kPa to 510 kPa, e.g., from 10 kPa to 450 kPa or from 50 kPa to 350 kPa. Although the temperature of second column 154 may vary, when at about 20 kPa to 70 kPa, the temperature of the second residue exiting in line 162 preferably is from 30° C. to 75° C., e.g., from 35° C. to 70° C. or from 40° C. to 65° C. The temperature of the second distillate exiting in line 161 preferably is from 20° C. to 55° C., e.g., from 25° C. to 50° C. or from 30° C. to 45° C.

The total concentration of water fed to second column 154 preferably is less than 10 wt. %, as discussed above. When first distillate in line 153 and/or ethanol mixture stream 160 comprises minor amounts of water, e.g., less than 1 wt. % or less than 0.5 wt. %, additional water may be fed to the second column 154 as an extractive agent in the upper portion of the column. A sufficient amount of water is preferably added via the extractive agent such that the total concentration of water fed to second column 154 is from 1 to 10 wt. % water, e.g., from 2 to 6 wt. %, based on the total weight of all components fed to second column 154. If the extractive agent comprises water, the water may be obtained from an external source or from an internal return/recycle line from one or more of the other columns or water separators.

Suitable extractive agents may also include, for example, dimethylsulfoxide, glycerine, diethylene glycol, 1-naphthol, hydroquinone, N,N'-dimethylformamide, 1,4-butanediol; ethylene glycol-1,5-pentanediol; propylene glycol-tetraethylene glycol-polyethylene glycol; glycerine-propylene glycol-tetraethylene glycol-1,4-butanediol, ethyl ether, methyl formate, cyclohexane, N,N'-dimethyl-1,3-propanediamine, N,N'-dimethylethylenediamine, diethylene triamine, hexamethylene diamine and 1,3-diaminopentane, an alkylated thiopene, dodecane, tridecane, tetradecane, chlorinated paraffins, or a combination thereof. When extractive agents are used, a suitable recovery system, such as a further distillation column, may be used to recycle the extractive agent.

Exemplary components for the second distillate and second residue compositions for the second column 154 are provided in Table 8, below. It should be understood that the distillate and residue may also contain other components, not listed in Table 8.

TABLE 8

SECOND COLUMN 154 (FIG. 4)

|  | Conc. (wt. %) | Conc. (wt. %) | Conc. (wt. %) |
|---|---|---|---|
| Second Distillate |  |  |  |
| Ethyl Acetate | 5 to 90 | 10 to 80 | 15 to 75 |
| Acetaldehyde | <60 | 1 to 40 | 1 to 35 |
| Ethanol | <45 | 0.001 to 40 | 0.01 to 35 |
| Water | <20 | 0.01 to 10 | 0.1 to 5 |
| Second Residue |  |  |  |
| Ethanol | 80 to 99.5 | 85 to 99.5 | 90 to 99.5 |
| Water | <20 | 0.001 to 15 | 0.01 to 10 |
| Ethyl Acetate | <1 | 0.001 to 2 | 0.001 to 0.5 |
| Acetic Acid | <0.5 | <0.01 | 0.001 to 0.01 |

The second distillate in line 161, which comprises ethyl acetate and/or acetaldehyde, preferably is refluxed as shown in FIG. 4, for example, at a reflux ratio from 1:30 to 30:1, e.g., from 1:10 to 10:1 or from 1:3 to 3:1. In one aspect, not shown, the second distillate 161 or a portion thereof may be returned to reaction zone 102. The ethyl acetate and/or acetaldehyde in the second distillate may be further reacted in reaction zone 102.

In optional embodiment, the second distillate in line 161 and/or a refined second distillate, or a portion of either or both streams, may be further separated to produce an acetaldehyde-containing stream and an ethyl acetate-containing stream similar to optional fourth column in FIG. 4. This may allow a portion of either the resulting acetaldehyde-containing stream or ethyl acetate-containing stream to be recycled to reactor 108 while purging the other stream. The purge stream may be valuable as a source of either ethyl acetate and/or acetaldehyde.

FIG. 5 illustrates another exemplary separation system used to produce ethanol from liquids stream 117. Liquid stream 117 is introduced in the upper part of first column 170, e.g., upper half or upper third. In one embodiment, no entrainers are added to first column 170. In first column 170, a weight majority of the ethanol, water, acetic acid, and other heavy components, if present, are removed from liquid stream 117 and are withdrawn, preferably continuously, as residue in line 171. First column 170 also forms an overhead distillate, which is withdrawn in line 172, and which may be condensed and refluxed, for example, at a ratio from 30:1 to 1:30, e.g., from 10:1 to 1:10 or from 1:5 to 5:1. The overhead distillate in stream 172 preferably comprises a weight majority of the ethyl acetate from liquid stream 117.

When column 170 is operated under about 170 kPa, the temperature of the residue exiting in line 171 preferably is from 70° C. to 155° C., e.g., from 90° C. to 130° C. or from 100° C. to 110° C. The base of column 170 may be maintained at a relatively low temperature by withdrawing a residue stream comprising ethanol, water, and acetic acid, thereby providing an energy efficiency advantage. The temperature of the distillate exiting in line 172 preferably at 170 kPa is from 75° C. to 100° C., e.g., from 75° C. to 83° C. or from 81° C. to 84° C. In some embodiments, the pressure of first column 170 may range from 0.1 kPa to 510 kPa, e.g., from 1 kPa to 475 kPa or from 1 kPa to 375 kPa. Exemplary components of the distillate and residue compositions for first column 170 are provided in Table 9 below. It should also be understood that the distillate and residue may also contain other components, not listed in Table 9.

TABLE 9

FIRST COLUMN 170 (FIG. 5)

|  | Conc. (wt. %) | Conc. (wt. %) | Conc. (wt. %) |
|---|---|---|---|
| Distillate |  |  |  |
| Ethyl Acetate | 10 to 85 | 15 to 80 | 20 to 75 |
| Acetaldehyde | 0.1 to 70 | 0.2 to 65 | 0.5 to 65 |
| Acetal | <0.1 | <0.1 | <0.05 |
| Acetone | <0.05 | 0.001 to 0.03 | 0.01 to 0.025 |
| Ethanol | 3 to 55 | 4 to 50 | 5 to 45 |
| Water | 0.1 to 20 | 1 to 15 | 2 to 10 |
| Acetic Acid | <2 | <0.1 | <0.05 |
| Residue |  |  |  |
| Acetic Acid | 0.01 to 35 | 0.1 to 30 | 0.2 to 25 |
| Water | 25 to 70 | 30 to 65 | 35 to 60 |
| Ethanol | 10 to 75 | 15 to 70 | 20 to 65 |

In an embodiment of the present invention, column 170 may be operated at a temperature where most of the water, ethanol, and acetic acid are removed from the residue stream and only a small amount of ethanol and water is collected in the distillate stream due to the formation of binary and tertiary azeotropes. The weight ratio of water in the residue in line 171 to water in the distillate in line 172 may be greater than 1:1, e.g., greater than 2:1. The weight ratio of ethanol in the residue to ethanol in the distillate may be greater than 1:1, e.g., greater than 2:1

The amount of acetic acid in the first residue may vary depending primarily on the conversion in reaction zone 102. In one embodiment, when the conversion is high, e.g., greater than 90%, the amount of acetic acid in the first residue may be less than 10 wt. %, e.g., less than 5 wt. % or less than 2 wt. %. In other embodiments, when the conversion is lower, e.g., less than 90%, the amount of acetic acid in the first residue may be greater than 10 wt. %.

The distillate preferably is substantially free of acetic acid, e.g., comprising less than 1000 wppm, less than 500 wppm or less than 100 wppm acetic acid. The distillate may be purged from the system or recycled in whole or part to reaction zone 102. In some embodiments, the distillate may be further separated, e.g., in a distillation column (not shown), into an acetaldehyde stream and an ethyl acetate stream. Either of these streams may be returned to the first reaction zone 102 or separated from system as a separate product.

Some species, such as acetals, may decompose in first column 170 such that very low amounts, or even no detectable amounts, of acetals remain in the distillate or residue.

To recover ethanol, the residue in line 171 may be further separated in a second column 173, also referred to as an "acid separation column." An acid separation column may be used when the acetic acid concentration in the first residue is greater than 1 wt. %, e.g., greater than 5 wt. %. The first residue in line 171 is introduced to second column 173 preferably in the top part of column 173, e.g., top half or top third. Second column 173 yields a second residue in line 174 comprising acetic acid and water, and a second distillate in line 175 comprising ethanol. Second column 173 may be a tray column or packed column. In one embodiment, second column 173 is a tray column having from 5 to 150 trays, e.g., from 15 to 50 trays or from 20 to 45 trays. Although the temperature and pressure of second column 173 may vary, when at atmospheric pressure the temperature of the second residue exiting in line 174 preferably is from 95° C. to 130° C., e.g., from 100° C. to 125° C. or from 110° C. to 120° C. The temperature of the second distillate exiting in line 175 preferably is from 60° C. to 105° C., e.g., from 75° C. to 100°

C. or from 80° C. to 100° C. The pressure of second column 173 may range from 0.1 kPa to 510 kPa, e.g., from 1 kPa to 475 kPa or from 1 kPa to 375 kPa. Exemplary components for the distillate and residue compositions for second column 173 are provided in Table 10 below. It should be understood that the distillate and residue may also contain other components, not listed in Table 10.

TABLE 10

SECOND COLUMN 173 (FIG. 5)

|  | Conc. (wt. %) | Conc. (wt. %) | Conc. (wt. %) |
|---|---|---|---|
| Second Distillate | | | |
| Ethanol | 70 to 99.9 | 75 to 98 | 80 to 95 |
| Ethyl Acetate | <10 | 0.001 to 5 | 0.01 to 3 |
| Acetaldehyde | <5 | 0.001 to 1 | 0.005 to 0.5 |
| Water | 0.1 to 30 | 1 to 25 | 5 to 20 |
| Second Residue | | | |
| Acetic Acid | 0.1 to 45 | 0.2 to 40 | 0.5 to 35 |
| Water | 45 to 100 | 55 to 99.8 | 65 to 99.5 |
| Ethyl Acetate | <2 | <1 | <0.5 |
| Ethanol | <5 | 0.001 to 5 | <2 |

The weight ratio of ethanol in the second distillate in line 175 to ethanol in the second residue in line 174 preferably is at least 35:1. In one embodiment, the weight ratio of water in the second residue 174 to water in the second distillate 175 is greater than 2:1, e.g., greater than 4:1 or greater than 6:1. In addition, the weight ratio of acetic acid in the second residue 174 to acetic acid in the second distillate 175 preferably is greater than 10:1, e.g., greater than 15:1 or greater than 20:1. Preferably, the second distillate in line 175 is substantially free of acetic acid and may only contain, if any, trace amounts of acetic acid. Preferably, the second distillate in line 175 contains substantially no ethyl acetate.

The remaining water from the second distillate in line 175 may be removed in further embodiments of the present invention. Depending on the water concentration, the ethanol product may be derived from the second distillate in line 175. Some applications, such as industrial ethanol applications, may tolerate water in the ethanol product, while other applications, such as fuel applications, may require an anhydrous ethanol. The amount of water in the distillate of line 175 may be closer to the azeotropic amount of water, e.g., at least 4 wt. %, preferably less than 20 wt. %, e.g., less than 12 wt. % or less than 7.5 wt. %. Water may be removed from the second distillate in line 175 using several different separation techniques as described herein. Particularly preferred techniques include the use of distillation column, membranes, adsorption units, and combinations thereof.

Some of the residues withdrawn from the separation systems shown in FIGS. 3, 4, and 5, may comprise acetic acid and water. Depending on the amount of water and acetic acid contained in the residue of first column or residue of second column, the residue may be treated in one or more of the following processes. The following are exemplary processes for further treating the residue and it should be understood that any of the following may be used regardless of acetic acid concentration. When the residue comprises a majority of acetic acid, e.g., greater than 70 wt. %, the residue may be recycled to the reactor without any separation of the water. In one embodiment, the residue may be separated into an acetic acid stream and a water stream when the residue comprises a majority of acetic acid, e.g., greater than 50 wt. %. Acetic acid may also be recovered in some embodiments from the residue having a lower acetic acid concentration. The residue may be separated into the acetic acid and water streams by a distillation column or one or more membranes. If a membrane or an array of membranes is employed to separate the acetic acid from the water, the membrane or array of membranes may be selected from any suitable acid resistant membrane that is capable of removing a permeate water stream. The resulting acetic acid stream optionally is returned to the reaction zone 102. The resulting water stream may be used as an extractive agent or to hydrolyze an ester-containing stream in a hydrolysis unit.

In other embodiments, for example, where the residue comprises less than 50 wt. % acetic acid, possible options include one or more of: (i) returning a portion of the residue to reactor 108, (ii) neutralizing the acetic acid, (iii) reacting the acetic acid with an alcohol, or (iv) disposing of the residue in a waste water treatment facility. It also may be possible to separate a residue comprising less than 50 wt. % acetic acid using a weak acid recovery distillation column to which a solvent (optionally acting as an azeotroping agent) may be added. Exemplary solvents that may be suitable for this purpose include ethyl acetate, propyl acetate, isopropyl acetate, butyl acetate, vinyl acetate, diisopropyl ether, carbon disulfide, tetrahydrofuran, isopropanol, ethanol, and $C_3$-$C_{12}$ alkanes. When neutralizing the acetic acid, it is preferred that the residue comprises less than 10 wt. % acetic acid. Acetic acid may be neutralized with any suitable alkali or alkaline earth metal base, such as sodium hydroxide or potassium hydroxide. When reacting acetic acid with an alcohol, it is preferred that the residue comprises less than 50 wt. % acetic acid. The alcohol may be any suitable alcohol, such as methanol, ethanol, propanol, butanol, or mixtures thereof. The reaction forms an ester that may be integrated with other systems, such as carbonylation production or an ester production process. Preferably, the alcohol comprises ethanol and the resulting ester comprises ethyl acetate. Optionally, the resulting ester may be fed to the hydrogenation reactor.

In some embodiments, when the residue comprises very minor amounts of acetic acid, e.g., less than 5 wt. %, the residue may be disposed of to a waste water treatment facility without further processing. The organic content, e.g., acetic acid content, of the residue beneficially may be suitable to feed microorganisms used in a waste water treatment facility.

The columns shown in figures may comprise any distillation column capable of performing the desired separation and/or purification. Each column preferably comprises a tray column having from 1 to 150 trays, e.g., from 10 to 100 trays, from 20 to 95 trays or from 30 to 75 trays. The trays may be sieve trays, fixed valve trays, movable valve trays, or any other suitable design known in the art. In other embodiments, a packed column may be used. For packed columns, structured packing or random packing may be employed. The trays or packing may be arranged in one continuous column or they may be arranged in two or more columns such that the vapor from the first section enters the second section while the liquid from the second section enters the first section, etc.

The associated condensers and liquid separation vessels that may be employed with each of the distillation columns may be of any conventional design and are simplified in the figures. Heat may be supplied to the base of each column or to a circulating bottom stream through a heat exchanger or reboiler. Other types of reboilers, such as internal reboilers, may also be used. The heat that is provided to the reboilers may be derived from any heat generated during the process that is integrated with the reboilers or from an external source such as another heat generating chemical process or a boiler. Although one reactor and one flasher are shown in the figures, additional reactors, flashers, condensers, heating elements, and other components may be used in various embodiments of the present invention. As will be recognized by those skilled in the art, various condensers, pumps, compressors, reboilers, drums, valves, connectors, separation vessels, etc., normally employed in carrying out chemical processes may also be combined and employed in the processes of the present invention.

The temperatures and pressures employed in the columns may vary. As a practical matter, pressures from 10 kPa to 3000 kPa will generally be employed in these zones although in some embodiments subatmospheric pressures or superatmospheric pressures may be employed. Temperatures within the various zones will normally range between the boiling points of the composition removed as the distillate and the composition removed as the residue. As will be recognized by those skilled in the art, the temperature at a given location in an operating distillation column is dependent on the composition of the material at that location and the pressure of column. In addition, feed rates may vary depending on the size of the production process and, if described, may be generically referred to in terms of feed weight ratios.

The final ethanol product produced by the processes of the present invention may be taken from a stream that primarily comprises ethanol from FIGS. 2, 3, and 4. The ethanol product may be an industrial grade ethanol comprising from 75 to 96 wt. % ethanol, e.g., from 80 to 96 wt. % or from 85 to 96 wt. % ethanol, based on the total weight of the ethanol product. Exemplary finished ethanol compositional ranges are provided below in Table 11.

TABLE 11

FINISHED ETHANOL COMPOSITIONS

| Component | Conc. (wt. %) | Conc. (wt. %) | Conc. (wt. %) |
|---|---|---|---|
| Ethanol | 75 to 96 | 80 to 96 | 85 to 96 |
| Water | <12 | 1 to 9 | 3 to 8 |
| Acetic Acid | <1 | <0.1 | <0.01 |
| Ethyl Acetate | <2 | <0.5 | <0.05 |
| Acetal | <0.05 | <0.01 | <0.005 |
| Acetone | <0.05 | <0.01 | <0.005 |
| Isopropanol | <0.5 | <0.1 | <0.05 |
| n-propanol | <0.5 | <0.1 | <0.05 |

The finished ethanol composition of the present invention preferably contains very low amounts, e.g., less than 0.5 wt. %, of other alcohols, such as methanol, butanol, isobutanol, isoamyl alcohol and other $C_4$-$C_{20}$ alcohols. In one embodiment, the amount of isopropanol in the finished ethanol composition is from 80 to 1,000 wppm, e.g., from 95 to 1,000 wppm, from 100 to 700 wppm, or from 150 to 500 wppm. In one embodiment, the finished ethanol composition is substantially free of acetaldehyde, optionally comprising less than 8 wppm acetaldehyde, e.g., less than 5 wppm or less than 1 wppm.

In some embodiments, when further water separation is used, the ethanol product may be withdrawn as a stream from the water separation unit as discussed above. In such embodiments, the ethanol concentration of the ethanol product may be greater than indicated in Table 11, and preferably is greater than 97 wt. % ethanol, e.g., greater than 98 wt. % or greater than 99.5 wt. %. The ethanol product in this aspect preferably comprises less than 3 wt. % water, e.g., less than 2 wt. % or less than 0.5 wt. %.

The finished ethanol composition produced by the embodiments of the present invention may be used in a variety of applications including fuels, solvents, chemical feedstocks, pharmaceutical products, cleansers, sanitizers, hydrogenation transport or consumption. In fuel applications, the finished ethanol composition may be blended with gasoline for motor vehicles such as automobiles, boats and small piston engine aircraft. In non-fuel applications, the finished ethanol composition may be used as a solvent for toiletry and cosmetic preparations, detergents, disinfectants, coatings, inks, and pharmaceuticals. The finished ethanol composition may also be used as a processing solvent in manufacturing processes for medicinal products, food preparations, dyes, photochemicals and latex processing.

The finished ethanol composition may also be used as a chemical feedstock to make other chemicals such as vinegar, ethyl acrylate, ethyl acetate, ethylene, glycol ethers, ethylamines, ethyl benzene, aldehydes, butadiene, and higher alcohols, especially butanol. In the production of ethyl acetate, the finished ethanol composition may be esterified with acetic acid. In another application, the finished ethanol composition may be dehydrated to produce ethylene. Any known dehydration catalyst can be employed to dehydrate ethanol, such as those described in copending U.S. Pub. Nos. 2010/0030002 and 2010/0030001, the entire contents and disclosures of which are hereby incorporated by reference. A zeolite catalyst, for example, may be employed as the dehydration catalyst. Preferably, the zeolite has a pore diameter of at least about 0.6 nm, and preferred zeolites include dehydration catalysts selected from the group consisting of mordenites, ZSM-5, a zeolite X and a zeolite Y. Zeolite X is described, for example, in U.S. Pat. No. 2,882,244 and zeolite Yin U.S. Pat. No. 3,130,007, the entireties of which are hereby incorporated herein by reference.

While the invention has been described in detail, modifications within the spirit and scope of the invention will be readily apparent to those of skill in the art. In view of the foregoing discussion, relevant knowledge in the art and references discussed above in connection with the Background and Detailed Description, the disclosures of which are all incorporated herein by reference. In addition, it should be understood that aspects of the invention and portions of various embodiments and various features recited below and/or in the appended claims may be combined or interchanged either in whole or in part. In the foregoing descriptions of the various embodiments, those embodiments which refer to another embodiment may be appropriately combined with other embodiments as will be appreciated by one of skill in the art. Furthermore, those of ordinary skill in the art will appreciate that the foregoing description is by way of example only, and is not intended to limit the invention.

We claim:

1. A process for producing ethanol, the steps comprising:
   separating at least a portion of a crude vinyl acetate mixture to yield a vinyl acetate product stream and a by-product stream comprising acetic acid, ethyl acetate, and vinyl acetate;
   hydrogenating at least a portion of the by-product stream in the presence of a catalyst to produce a crude ethanol product; and
   recovering ethanol from the crude ethanol product.

2. The process of claim 1, wherein the by-product stream further comprises vinyl proprionate in an amount of less than 2 wt. %.

3. The process of claim 1, wherein the by-product stream comprises from 0.01 to 50 wt. % ethyl acetate.

4. The process of claim 1, wherein the by-product stream comprises less than 98 wt. % acetic acid.

5. The process of claim 1, wherein the by-product stream comprises from 0.01 to 35 wt. % vinyl acetate.

6. The process of claim 1, further comprising enriching the by-product stream with acetic acid and/or ethyl acetate, wherein the total concentration of acetic acid and/or ethyl acetate in the enriched by-product stream is greater than 70 wt. %.

7. The process of claim 1, further comprising combining the by-product stream with a feed stream comprising acetic acid and/or ethyl acetate, and further comprising hydrogenating the combined streams to produce ethanol.

8. The process of claim 1, further comprising the step of: removing vinyl acetate from the by-product stream to provide a treated stream and hydrogenating a portion of the treated stream.

9. The process of claim 1, wherein the crude vinyl acetate mixture is derived from a reaction product of ethylene, acetic acid, and oxygen.

10. The process of claim 1, wherein the catalyst comprises a combination metals selected from the group consisting of platinum/tin, platinum/ruthenium, platinum/rhenium, palladium/ruthenium, palladium/rhenium, cobalt/palladium, cobalt/platinum, cobalt/chromium, cobalt/ruthenium, silver/palladium, copper/palladium, nickel/palladium, gold/palladium, ruthenium/rhenium, and ruthenium/iron.

11. The process of claim 1, wherein the crude ethanol product comprises ethanol, ethyl acetate, aldehyde, and water.

12. A process for producing ethanol, the steps comprising:
providing a by-product stream comprising acetic acid, ethyl acetate, and vinyl acetate;
hydrogenating at least a portion of the by-product stream in the presence of a catalyst to produce a crude ethanol product; and
recovering ethanol from the crude ethanol product.

13. A process for producing ethanol, the steps comprising:
separating at least a portion of a crude vinyl acetate mixture in an azeotrope column to yield a vinyl acetate product stream and sidestream comprising acetic acid and ethyl acetate;
hydrogenating at least a portion of the sidestream in the presence of a catalyst to produce a crude ethanol product; and
recovering ethanol from the crude ethanol product.

14. The process of claim 13, wherein the sidestream further comprises vinyl proprionate in an amount of less than 2 wt. %.

15. The process of claim 13, wherein the sidestream further comprises vinyl acetate in an amount from 0.01 to 35 wt. % vinyl acetate.

16. The process of claim 13, wherein the sidestream comprises from 30 to 80 wt. % acetic acid.

17. The process of claim 13, further comprising combining the sidestream with a feed stream comprising acetic acid and/or ethyl acetate, and further comprising hydrogenating the combined streams to produce ethanol.

18. The process of claim 13, further comprising separating a bottom stream comprising acetic acid from the azeotrope column.

19. A process for producing ethanol, the steps comprising:
separating at least a portion of a crude vinyl acetate mixture in an azeotrope column to yield a vinyl acetate product stream and bottom stream comprising ethyl acetate and acetic acid;
hydrogenating at least a portion of the bottom stream in the presence of a catalyst to produce a crude ethanol product; and
recovering ethanol from the crude ethanol product.

20. The process of claim 19, wherein the bottom stream further comprises vinyl proprionate in an amount of less 2 wt. %.

21. The process of claim 19, wherein the bottom stream further comprises vinyl acetate in an amount from 0.01 to 35 wt. % vinyl acetate.

22. The process of claim 21, further comprising the step of: removing vinyl acetate from the bottom stream to provide a treated bottom stream and hydrogenating a portion of the treated bottom stream.

23. The process of claim 19, wherein the bottom stream comprises from 50 to 98 wt. % acetic acid and from 0.01 to 50 wt. % ethyl acetate.

24. The process of claim 19, further comprising enriching the bottom stream with acetic acid and/or ethyl acetate, wherein the total concentration of acetic acid and/or ethyl acetate in the enriched bottom stream is greater than 70 wt. %.

25. The process of claim 19, further comprising combining the bottom stream with a feed stream comprising acetic acid and/or ethyl acetate, and further comprising hydrogenating the combined streams to produce ethanol.

\* \* \* \* \*